US012029426B2

(12) United States Patent
Millman et al.

(10) Patent No.: US 12,029,426 B2
(45) Date of Patent: Jul. 9, 2024

(54) ENDOSCOPIC PURSE STRING SUTURE SURGICAL DEVICE

(71) Applicant: INTUITIVE SURGICAL OPERATIONS, INC., Sunnyvale, CA (US)

(72) Inventors: Paul Millman, San Jose, CA (US); William Burbank, Sandy Hook, CT (US); Nina Frankel, San Jose, CA (US); Steven D. Wexner, Parkland, FL (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 510 days.

(21) Appl. No.: 17/281,578

(22) PCT Filed: Oct. 18, 2019

(86) PCT No.: PCT/US2019/056979
§ 371 (c)(1),
(2) Date: Mar. 30, 2021

(87) PCT Pub. No.: WO2020/081960
PCT Pub. Date: Apr. 23, 2020

(65) Prior Publication Data
US 2021/0386427 A1     Dec. 16, 2021

Related U.S. Application Data

(60) Provisional application No. 62/747,912, filed on Oct. 19, 2018.

(51) Int. Cl.
*A61B 17/115* (2006.01)
*A61B 17/00* (2006.01)
(Continued)

(52) U.S. Cl.
CPC .... *A61B 17/115* (2013.01); *A61B 2017/00367* (2013.01); *A61B 2017/1142* (2013.01); *A61B 34/37* (2016.02)

(58) Field of Classification Search
CPC ............ A61B 17/07207; A61B 17/115; A61B 17/0682; A61B 34/30; A61B 34/74;
(Continued)

(56) References Cited

U.S. PATENT DOCUMENTS

| 4,305,539 A | 12/1981 | Korolkov et al. |
| 4,319,576 A | 3/1982 | Rothfuss |

(Continued)

FOREIGN PATENT DOCUMENTS

| CN | 112165909 A | 1/2021 |
| EP | 0277532 B1 | 8/1990 |

(Continued)

OTHER PUBLICATIONS

International Search Report and Written Opinion for Application No. PCT/US2020/054568, mailed Jan. 29, 2021, 13 pages.

(Continued)

*Primary Examiner* — Thomas M Wittenschlaeger
(74) *Attorney, Agent, or Firm* — Farber LLC

(57) ABSTRACT

A surgical stapler for applying a suture to tissue includes a first jaw and a second jaw configured to receive a cartridge. An actuation mechanism translates a drive member distally through the first and second jaws to apply staples to tissue such that a suture, in combination with the staples, forms a purse string when the stapler activated. The cartridge includes a first upper portion and a second lower portion.

16 Claims, 23 Drawing Sheets

(51) Int. Cl.
*A61B 17/11* (2006.01)
*A61B 34/37* (2016.01)
(58) Field of Classification Search
CPC .......... A61B 34/37; A61B 2017/1142; A61B 2017/0464; A61B 2017/07278; A61B 2017/07271; A61B 2017/07285; A61B 2017/00477; A61B 2017/2943; A61B 2017/0409; A61B 2017/00367; A61B 2034/302

See application file for complete search history.

(56) References Cited

U.S. PATENT DOCUMENTS

| | | | |
|---|---|---|---|
| 4,407,286 A | 10/1983 | Noiles et al. | |
| 4,429,695 A | 2/1984 | Green | |
| 4,509,518 A | 4/1985 | McGarry et al. | |
| 4,605,001 A | 8/1986 | Rothfuss et al. | |
| 4,608,981 A | 9/1986 | Rothfuss et al. | |
| 4,610,383 A | 9/1986 | Rothfuss et al. | |
| 4,633,874 A | 1/1987 | Chow et al. | |
| 4,767,044 A | 8/1988 | Green | |
| 4,809,695 A | 3/1989 | Gwathmey et al. | |
| 4,848,637 A | 7/1989 | Pruitt | |
| 4,892,244 A | 1/1990 | Fox et al. | |
| 4,930,503 A | 6/1990 | Pruitt | |
| 4,978,049 A | 12/1990 | Green | |
| 5,027,834 A | 7/1991 | Pruitt | |
| 5,040,715 A | 8/1991 | Green et al. | |
| 5,133,735 A | 7/1992 | Slater et al. | |
| 5,133,736 A | 7/1992 | Bales, Jr. et al. | |
| 5,147,357 A | 9/1992 | Rose et al. | |
| 5,180,092 A | 1/1993 | Crainich | |
| 5,275,323 A | 1/1994 | Schulze et al. | |
| 5,307,976 A | 5/1994 | Olson et al. | |
| 5,312,023 A | 5/1994 | Green et al. | |
| 5,334,183 A | 8/1994 | Wuchinich | |
| 5,342,395 A | 8/1994 | Jarrett et al. | |
| 5,342,396 A | 8/1994 | Cook | |
| 5,366,133 A | 11/1994 | Geiste | |
| 5,452,836 A | 9/1995 | Huitema et al. | |
| 5,452,837 A | 9/1995 | Williamson, IV et al. | |
| 5,465,895 A | 11/1995 | Knodel et al. | |
| 5,480,089 A | 1/1996 | Blewett | |
| 5,484,095 A | 1/1996 | Green et al. | |
| 5,484,451 A | 1/1996 | Akopov et al. | |
| 5,487,500 A | 1/1996 | Knodel et al. | |
| 5,497,931 A | 3/1996 | Nakamura | |
| 5,533,521 A | 7/1996 | Granger | |
| 5,540,375 A | 7/1996 | Bolanos et al. | |
| 5,554,164 A | 9/1996 | Wilson et al. | |
| 5,560,530 A | 10/1996 | Bolanos et al. | |
| 5,562,239 A | 10/1996 | Boiarski et al. | |
| 5,564,615 A | 10/1996 | Bishop et al. | |
| 5,571,116 A | 11/1996 | Bolanos et al. | |
| 5,571,285 A | 11/1996 | Chow et al. | |
| 5,573,534 A | 11/1996 | Stone | |
| 5,615,820 A | 4/1997 | Viola | |
| 5,624,452 A | 4/1997 | Yates | |
| 5,628,446 A | 5/1997 | Geiste et al. | |
| 5,651,491 A | 7/1997 | Heaton et al. | |
| 5,652,849 A | 7/1997 | Conway et al. | |
| 5,667,626 A | 9/1997 | Cayford et al. | |
| 5,673,840 A * | 10/1997 | Schulze .......... | A61B 17/07207 227/176.1 |
| 5,673,842 A | 10/1997 | Bittner et al. | |
| 5,676,674 A | 10/1997 | Bolanos et al. | |
| 5,688,269 A | 11/1997 | Newton et al. | |
| 5,690,269 A | 11/1997 | Bolanos et al. | |
| 5,693,042 A | 12/1997 | Boiarski et al. | |
| 5,697,542 A | 12/1997 | Knodel et al. | |
| 5,700,270 A | 12/1997 | Peyser et al. | |
| 5,700,276 A | 12/1997 | Benecke | |
| 5,709,680 A | 1/1998 | Yates et al. | |
| 5,752,644 A | 5/1998 | Bolanos et al. | |
| 5,752,973 A | 5/1998 | Kieturakis et al. | |
| 5,762,255 A | 6/1998 | Chrisman et al. | |
| 5,762,256 A | 6/1998 | Mastri et al. | |
| 5,779,130 A | 7/1998 | Alesi et al. | |
| 5,782,396 A | 7/1998 | Mastri et al. | |
| 5,792,135 A | 8/1998 | Madhani et al. | |
| 5,820,009 A | 10/1998 | Melling et al. | |
| 5,826,776 A | 10/1998 | Schulze et al. | |
| 5,833,695 A * | 11/1998 | Yoon .............. | A61B 17/07207 227/176.1 |
| 5,865,361 A | 2/1999 | Milliman et al. | |
| 5,871,135 A | 2/1999 | Williamson, IV et al. | |
| 5,911,353 A | 6/1999 | Bolanos et al. | |
| 5,915,616 A | 6/1999 | Viola et al. | |
| 5,919,198 A | 7/1999 | Graves, Jr. et al. | |
| 5,941,442 A | 8/1999 | Geiste et al. | |
| 5,954,259 A | 9/1999 | Viola et al. | |
| 5,959,892 A | 9/1999 | Lin et al. | |
| 6,032,849 A | 3/2000 | Mastri et al. | |
| 6,050,996 A | 4/2000 | Schmaltz et al. | |
| 6,079,606 A | 6/2000 | Milliman et al. | |
| 6,174,309 B1 | 1/2001 | Wrublewski et al. | |
| 6,202,914 B1 | 3/2001 | Geiste et al. | |
| 6,241,139 B1 | 6/2001 | Milliman et al. | |
| 6,250,532 B1 | 6/2001 | Green et al. | |
| 6,330,956 B1 | 12/2001 | Willinger | |
| 6,330,965 B1 | 12/2001 | Milliman et al. | |
| 6,488,196 B1 | 12/2002 | Fenton, Jr. | |
| 6,503,259 B2 | 1/2003 | Huxel et al. | |
| 6,585,735 B1 | 7/2003 | Frazier et al. | |
| 6,644,532 B2 | 11/2003 | Green et al. | |
| 6,656,193 B2 | 12/2003 | Grant et al. | |
| 6,669,073 B2 | 12/2003 | Milliman et al. | |
| 6,786,382 B1 | 9/2004 | Hoffman | |
| 6,817,974 B2 | 11/2004 | Cooper et al. | |
| 6,877,647 B2 | 4/2005 | Green et al. | |
| 6,905,057 B2 | 6/2005 | Swayze et al. | |
| 6,953,139 B2 | 10/2005 | Milliman et al. | |
| 6,959,852 B2 | 11/2005 | Shelton, IV et al. | |
| 6,964,363 B2 | 11/2005 | Wales et al. | |
| 6,978,921 B2 | 12/2005 | Shelton, IV et al. | |
| 6,978,922 B2 | 12/2005 | Bilotti et al. | |
| 6,986,451 B1 | 1/2006 | Mastri et al. | |
| 6,988,649 B2 | 1/2006 | Shelton, IV et al. | |
| 7,000,818 B2 | 2/2006 | Shelton, IV et al. | |
| 7,000,819 B2 | 2/2006 | Swayze et al. | |
| 7,044,352 B2 | 5/2006 | Shelton, IV et al. | |
| 7,044,353 B2 | 5/2006 | Mastri et al. | |
| 7,055,731 B2 | 6/2006 | Shelton, IV et al. | |
| 7,059,508 B2 | 6/2006 | Shelton, IV et al. | |
| 7,070,083 B2 | 7/2006 | Jankowski | |
| 7,114,642 B2 | 10/2006 | Whitman | |
| 7,128,253 B2 | 10/2006 | Mastri et al. | |
| 7,140,527 B2 | 11/2006 | Ehrenfels et al. | |
| 7,140,528 B2 | 11/2006 | Shelton, IV et al. | |
| 7,258,262 B2 | 8/2007 | Mastri et al. | |
| 7,308,998 B2 | 12/2007 | Mastri et al. | |
| 7,328,828 B2 | 2/2008 | Ortiz et al. | |
| 7,380,695 B2 | 6/2008 | Doll et al. | |
| 7,380,696 B2 | 6/2008 | Shelton, IV et al. | |
| 7,398,908 B2 | 7/2008 | Holsten et al. | |
| 7,401,721 B2 | 7/2008 | Holsten et al. | |
| 7,407,075 B2 | 8/2008 | Holsten et al. | |
| 7,455,676 B2 | 11/2008 | Holsten et al. | |
| 7,472,814 B2 | 1/2009 | Mastri et al. | |
| 7,481,349 B2 | 1/2009 | Holsten et al. | |
| 7,494,039 B2 | 2/2009 | Racenet et al. | |
| 7,565,993 B2 | 7/2009 | Milliman et al. | |
| 7,588,174 B2 | 9/2009 | Holsten et al. | |
| 7,654,431 B2 | 2/2010 | Hueil et al. | |
| 7,658,312 B2 | 2/2010 | Vidal et al. | |
| 7,673,783 B2 | 3/2010 | Morgan et al. | |
| 7,699,835 B2 | 4/2010 | Lee et al. | |
| 7,721,930 B2 | 5/2010 | McKenna et al. | |
| 7,726,539 B2 | 6/2010 | Holsten et al. | |
| 7,770,774 B2 | 8/2010 | Mastri et al. | |
| 7,794,475 B2 | 9/2010 | Hess et al. | |
| 7,832,611 B2 | 11/2010 | Boyden et al. | |
| 7,837,079 B2 | 11/2010 | Holsten et al. | |

(56) References Cited

U.S. PATENT DOCUMENTS

| | | |
|---|---|---|
| 7,866,526 B2 | 1/2011 | Green et al. |
| 7,942,303 B2 | 5/2011 | Shah et al. |
| 7,950,561 B2 | 5/2011 | Aranyi |
| 8,070,035 B2 | 12/2011 | Holsten et al. |
| 8,083,118 B2 | 12/2011 | Milliman et al. |
| 8,127,975 B2 | 3/2012 | Olson et al. |
| 8,157,152 B2 | 4/2012 | Holsten et al. |
| 8,272,553 B2 | 9/2012 | Mastri et al. |
| 8,308,042 B2 | 11/2012 | Aranyi |
| 8,348,127 B2 | 1/2013 | Marczyk |
| 8,365,972 B2 | 2/2013 | Aranyi et al. |
| 8,371,492 B2 | 2/2013 | Aranyi et al. |
| 8,439,246 B1 | 5/2013 | Knodel |
| 8,490,851 B2 | 7/2013 | Blier et al. |
| 8,551,091 B2 | 10/2013 | Couture et al. |
| 8,573,465 B2 | 11/2013 | Shelton, IV |
| 8,579,178 B2 | 11/2013 | Holsten et al. |
| 8,608,047 B2 | 12/2013 | Holsten et al. |
| 8,672,939 B2 | 3/2014 | Garrison |
| 8,701,960 B1 | 4/2014 | Manoux et al. |
| 8,783,541 B2 | 7/2014 | Shelton, IV et al. |
| 8,800,841 B2 | 8/2014 | Ellerhorst et al. |
| 8,858,547 B2 | 10/2014 | Brogna |
| 8,864,010 B2 | 10/2014 | Williams |
| 8,905,287 B2 | 12/2014 | Racenet et al. |
| 8,925,785 B2 | 1/2015 | Holsten et al. |
| 9,010,606 B2 | 4/2015 | Aranyi et al. |
| 9,055,961 B2 | 6/2015 | Manzo et al. |
| 9,192,378 B2 | 11/2015 | Aranyi et al. |
| 9,192,379 B2 | 11/2015 | Aranyi et al. |
| 9,211,120 B2 | 12/2015 | Scheib et al. |
| 9,216,019 B2 | 12/2015 | Schmid et al. |
| 9,345,479 B2 | 5/2016 | Racenet et al. |
| 9,717,497 B2 | 8/2017 | Zerkle et al. |
| 9,717,498 B2 | 8/2017 | Aranyi et al. |
| 9,936,949 B2 | 4/2018 | Measamer et al. |
| 10,111,659 B2 | 10/2018 | Racenet et al. |
| 10,130,367 B2 | 11/2018 | Cappola et al. |
| 10,231,732 B1 | 3/2019 | Racenet et al. |
| 10,285,693 B2 | 5/2019 | Kimsey et al. |
| 10,646,219 B2 | 5/2020 | Racenet et al. |
| 10,828,027 B2 | 11/2020 | Racenet et al. |
| 10,863,988 B2 | 12/2020 | Patel et al. |
| 11,234,700 B2 | 2/2022 | Ragosta et al. |
| 11,439,390 B2 | 9/2022 | Patel et al. |
| 11,504,124 B2 | 11/2022 | Patel et al. |
| 11,517,312 B2 | 12/2022 | Wixey |
| 11,642,129 B2 | 5/2023 | Burbank |
| 11,723,661 B2 | 8/2023 | Wixey et al. |
| 2002/0165562 A1 | 11/2002 | Grant et al. |
| 2003/0135204 A1 | 7/2003 | Lee et al. |
| 2003/0181910 A1 | 9/2003 | Dycus et al. |
| 2004/0232199 A1 | 11/2004 | Shelton et al. |
| 2004/0267310 A1 | 12/2004 | Racenet et al. |
| 2005/0006430 A1 | 1/2005 | Wales |
| 2005/0006434 A1 | 1/2005 | Wales et al. |
| 2005/0070925 A1 | 3/2005 | Shelton, IV et al. |
| 2005/0070958 A1 | 3/2005 | Swayze et al. |
| 2005/0101991 A1 | 5/2005 | Ahlberg et al. |
| 2005/0113826 A1 | 5/2005 | Johnson et al. |
| 2005/0178813 A1 | 8/2005 | Swayze et al. |
| 2005/0187576 A1 | 8/2005 | Whitman et al. |
| 2005/0273084 A1 | 12/2005 | Hinman et al. |
| 2005/0273085 A1 | 12/2005 | Hinman et al. |
| 2006/0000868 A1 | 1/2006 | Shelton, IV et al. |
| 2006/0016853 A1 | 1/2006 | Racenet |
| 2006/0022014 A1 | 2/2006 | Shelton, IV et al. |
| 2006/0022015 A1 | 2/2006 | Shelton et al. |
| 2006/0024817 A1 | 2/2006 | Deguchi et al. |
| 2006/0025809 A1 | 2/2006 | Shelton, IV |
| 2006/0025810 A1 | 2/2006 | Shelton, IV |
| 2006/0025811 A1 | 2/2006 | Shelton, IV |
| 2006/0025812 A1 | 2/2006 | Shelton, IV |
| 2006/0025813 A1 | 2/2006 | Shelton et al. |
| 2006/0025816 A1 | 2/2006 | Shelton, IV |
| 2006/0049230 A1 | 3/2006 | Shelton, IV et al. |
| 2006/0097026 A1 | 5/2006 | Shelton, IV |
| 2006/0111209 A1 | 5/2006 | Hinman et al. |
| 2006/0111210 A1 | 5/2006 | Hinman |
| 2006/0161190 A1 | 7/2006 | Gadberry et al. |
| 2006/0190031 A1 | 8/2006 | Wales et al. |
| 2006/0217706 A1 | 9/2006 | Lau et al. |
| 2006/0226196 A1 | 10/2006 | Hueil et al. |
| 2007/0010838 A1 | 1/2007 | Shelton, IV et al. |
| 2007/0045379 A1 | 3/2007 | Shelton, IV |
| 2007/0250113 A1 | 10/2007 | Hegeman et al. |
| 2007/0262116 A1 | 11/2007 | Hueil et al. |
| 2008/0023522 A1 | 1/2008 | Olson et al. |
| 2008/0078804 A1 | 4/2008 | Shelton et al. |
| 2008/0086114 A1 | 4/2008 | Schmitz et al. |
| 2008/0308607 A1 | 12/2008 | Timm et al. |
| 2009/0277947 A1 | 11/2009 | Viola |
| 2010/0006620 A1 | 1/2010 | Sorrentino et al. |
| 2010/0076474 A1 | 3/2010 | Yates et al. |
| 2010/0108740 A1 | 5/2010 | Pastorelli et al. |
| 2010/0145334 A1 | 6/2010 | Olson et al. |
| 2010/0179545 A1 | 7/2010 | Twomey et al. |
| 2010/0198248 A1 | 8/2010 | Vakharia |
| 2010/0331857 A1 | 12/2010 | Doyle et al. |
| 2011/0022078 A1 | 1/2011 | Hinman |
| 2011/0036891 A1 | 2/2011 | Zemlok et al. |
| 2011/0118707 A1 | 5/2011 | Burbank |
| 2011/0121050 A1 | 5/2011 | Nicholas et al. |
| 2011/0152879 A1 | 6/2011 | Williams |
| 2011/0174863 A1 | 7/2011 | Shelton, IV et al. |
| 2011/0251612 A1 | 10/2011 | Faller et al. |
| 2011/0251613 A1 | 10/2011 | Guerra et al. |
| 2011/0288573 A1 | 11/2011 | Yates et al. |
| 2011/0290851 A1 | 12/2011 | Shelton, IV |
| 2011/0290854 A1 | 12/2011 | Timm et al. |
| 2011/0295270 A1 | 12/2011 | Giordano et al. |
| 2011/0301603 A1 | 12/2011 | Kerr et al. |
| 2012/0000962 A1 | 1/2012 | Racenet et al. |
| 2012/0022584 A1 | 1/2012 | Donnigan et al. |
| 2012/0071891 A1 | 3/2012 | Itkowitz et al. |
| 2012/0223121 A1 | 9/2012 | Viola et al. |
| 2012/0228358 A1 | 9/2012 | Zemlok et al. |
| 2012/0248167 A1 | 10/2012 | Flanagan et al. |
| 2012/0255986 A1 | 10/2012 | Petty et al. |
| 2012/0289999 A1 | 11/2012 | Frank |
| 2012/0298719 A1* | 11/2012 | Shelton, IV ........... A61B 34/30 227/176.1 |
| 2013/0015231 A1 | 1/2013 | Kostrzewski |
| 2013/0046303 A1 | 2/2013 | Evans et al. |
| 2013/0056521 A1 | 3/2013 | Swensgard |
| 2013/0068821 A1 | 3/2013 | Huitema et al. |
| 2013/0087599 A1* | 4/2013 | Krumanaker ........ A61B 17/072 227/176.1 |
| 2013/0098965 A1 | 4/2013 | Kostrzewski et al. |
| 2013/0126586 A1 | 5/2013 | Zhang et al. |
| 2013/0148577 A1 | 6/2013 | Terry et al. |
| 2013/0248577 A1 | 9/2013 | Leimbach et al. |
| 2013/0277410 A1 | 10/2013 | Fernandez et al. |
| 2013/0296922 A1 | 11/2013 | Allen, IV et al. |
| 2013/0327808 A1 | 12/2013 | Chen et al. |
| 2014/0001236 A1 | 1/2014 | Shelton, IV et al. |
| 2014/0005653 A1 | 1/2014 | Shelton, IV et al. |
| 2014/0021239 A1 | 1/2014 | Kostrzewski |
| 2014/0025071 A1 | 1/2014 | Sims et al. |
| 2014/0100600 A1 | 4/2014 | Kendrick |
| 2014/0175152 A1 | 6/2014 | Hess et al. |
| 2014/0180286 A1 | 6/2014 | Marczyk et al. |
| 2014/0183244 A1 | 7/2014 | Duque et al. |
| 2014/0200596 A1 | 7/2014 | Weir et al. |
| 2014/0214049 A1 | 7/2014 | Jeong et al. |
| 2014/0257331 A1 | 9/2014 | Kim et al. |
| 2014/0263546 A1 | 9/2014 | Aranyi |
| 2014/0263559 A1 | 9/2014 | Williams et al. |
| 2014/0263567 A1 | 9/2014 | Williams et al. |
| 2014/0263569 A1 | 9/2014 | Williams et al. |
| 2014/0284372 A1 | 9/2014 | Kostrzewski |
| 2014/0343550 A1 | 11/2014 | Faller et al. |
| 2014/0343569 A1 | 11/2014 | Turner |
| 2014/0364851 A1 | 12/2014 | Batross et al. |

(56) References Cited

U.S. PATENT DOCUMENTS

| | | |
|---|---|---|
| 2015/0173789 A1 | 6/2015 | Baxter, III et al. |
| 2015/0209037 A1 | 7/2015 | Kostrzewski et al. |
| 2015/0250530 A1 | 9/2015 | Manzo et al. |
| 2015/0256609 A1 | 9/2015 | Morton et al. |
| 2015/0272575 A1 | 10/2015 | Leimbach et al. |
| 2015/0272576 A1 | 10/2015 | Cappola |
| 2015/0297227 A1 | 10/2015 | Huitema et al. |
| 2015/0297235 A1 | 10/2015 | Harris et al. |
| 2016/0038227 A1 | 2/2016 | Garrison |
| 2016/0058450 A1 | 3/2016 | Shelton, IV et al. |
| 2016/0066916 A1 | 3/2016 | Overmyer et al. |
| 2016/0089148 A1 | 3/2016 | Harris et al. |
| 2016/0120544 A1 | 5/2016 | Shelton, IV et al. |
| 2016/0157863 A1 | 6/2016 | Williams et al. |
| 2016/0174977 A1 | 6/2016 | Lytle, IV et al. |
| 2016/0175033 A1 | 6/2016 | Le |
| 2016/0192999 A1 | 7/2016 | Stulen et al. |
| 2016/0235489 A1 | 8/2016 | Gombert et al. |
| 2016/0249921 A1 | 9/2016 | Cappola et al. |
| 2016/0270780 A1 | 9/2016 | Hall et al. |
| 2016/0287251 A1 | 10/2016 | Shelton, IV et al. |
| 2016/0338764 A1 | 11/2016 | Krastins et al. |
| 2017/0010578 A1 | 1/2017 | Miyakawa |
| 2017/0042604 A1 | 2/2017 | McFarland et al. |
| 2017/0079710 A1 | 3/2017 | Deville et al. |
| 2017/0097035 A1 | 4/2017 | Zimmerman et al. |
| 2017/0135746 A1 | 5/2017 | Tetzlaff et al. |
| 2017/0189028 A1 | 7/2017 | Aranyi |
| 2017/0231653 A1 | 8/2017 | Kapadia |
| 2017/0245857 A1 | 8/2017 | Shelton, IV et al. |
| 2017/0290584 A1 | 10/2017 | Jasemian et al. |
| 2017/0296172 A1 | 10/2017 | Harris et al. |
| 2017/0296173 A1 | 10/2017 | Shelton, IV et al. |
| 2018/0008265 A1 | 1/2018 | Hatanaka et al. |
| 2018/0021042 A1 | 1/2018 | Nicholas et al. |
| 2018/0161052 A1 | 6/2018 | Weir et al. |
| 2018/0168581 A1 | 6/2018 | Hunter et al. |
| 2018/0168622 A1 | 6/2018 | Shelton, IV et al. |
| 2018/0168628 A1 | 6/2018 | Hunter et al. |
| 2018/0168637 A1 | 6/2018 | Harris et al. |
| 2018/0168641 A1 | 6/2018 | Harris et al. |
| 2018/0168642 A1 | 6/2018 | Shelton, IV et al. |
| 2018/0168649 A1 | 6/2018 | Shelton, IV et al. |
| 2018/0168650 A1 | 6/2018 | Shelton, IV et al. |
| 2018/0206844 A1 | 7/2018 | Harris et al. |
| 2018/0214200 A1 | 8/2018 | Nanditale et al. |
| 2018/0232951 A1 | 8/2018 | Alterovitz et al. |
| 2018/0296213 A1 | 10/2018 | Strobl |
| 2018/0310948 A1 | 11/2018 | Stamm et al. |
| 2018/0317915 A1 | 11/2018 | McDonald, II |
| 2019/0000454 A1 | 1/2019 | Swayze et al. |
| 2019/0015124 A1 | 1/2019 | Williams et al. |
| 2019/0059894 A1 | 2/2019 | Kumada et al. |
| 2019/0083086 A1 | 3/2019 | Klaffenböck et al. |
| 2019/0099181 A1 | 4/2019 | Shelton, IV et al. |
| 2019/0125347 A1 | 5/2019 | Stokes et al. |
| 2019/0133571 A1 | 5/2019 | Racenet et al. |
| 2019/0142531 A1 | 5/2019 | Wentworth et al. |
| 2019/0201146 A1 | 7/2019 | Shelton, IV et al. |
| 2019/0231350 A1 | 8/2019 | Scott et al. |
| 2019/0239881 A1 | 8/2019 | Laurent et al. |
| 2019/0290374 A1 | 9/2019 | Ramadorai |
| 2019/0298356 A1 | 10/2019 | Shelton, IV et al. |
| 2019/0314107 A1 | 10/2019 | Worrell et al. |
| 2019/0365458 A1 | 12/2019 | Whitlock et al. |
| 2020/0397430 A1 | 12/2020 | Patel et al. |
| 2021/0000557 A1 | 1/2021 | Mustufa et al. |
| 2021/0022736 A1 | 1/2021 | Wixey |
| 2021/0077101 A1 | 3/2021 | Patel et al. |
| 2021/0177495 A1 | 6/2021 | Ross et al. |
| 2021/0177500 A1 | 6/2021 | Khalaji |
| 2021/0212683 A1 | 7/2021 | Burbank |
| 2021/0267596 A1 | 9/2021 | Fanelli et al. |
| 2022/0015762 A1 | 1/2022 | Wixey et al. |
| 2022/0015763 A1 | 1/2022 | Wixey et al. |
| 2022/0015823 A1 | 1/2022 | Wilson et al. |
| 2022/0054130 A1 | 2/2022 | Overmyer et al. |
| 2022/0061836 A1 | 3/2022 | Parihar et al. |
| 2022/0061840 A1 | 3/2022 | Hites |
| 2022/0061841 A1 | 3/2022 | Wixey et al. |
| 2022/0071632 A1 | 3/2022 | Patel et al. |
| 2022/0079585 A1 | 3/2022 | Egan |
| 2022/0125428 A1 | 4/2022 | Ragosta et al. |
| 2022/0160358 A1 | 5/2022 | Wixey |
| 2022/0183686 A1 | 6/2022 | Wixey et al. |
| 2022/0192665 A1 | 6/2022 | Wellman |
| 2022/0346790 A1 | 11/2022 | Wellman |
| 2022/0378537 A1 | 12/2022 | Hites et al. |
| 2022/0395270 A1 | 12/2022 | Patel et al. |
| 2023/0020577 A1 | 1/2023 | Kerver et al. |
| 2023/0047784 A1 | 2/2023 | Patel et al. |
| 2023/0052074 A1 | 2/2023 | Wixey |
| 2023/0225731 A1 | 7/2023 | Burbank |

FOREIGN PATENT DOCUMENTS

| | | |
|---|---|---|
| EP | 0277529 B1 | 4/1993 |
| EP | 0641546 A1 | 3/1995 |
| EP | 1090592 A1 | 4/2001 |
| EP | 1728473 A1 | 12/2006 |
| EP | 1479346-81 | 1/2007 |
| EP | 1621141-81 | 7/2007 |
| EP | 1316290 B1 | 2/2012 |
| EP | 1754445-81 | 10/2013 |
| EP | 2777530 A1 | 9/2014 |
| EP | 2777532 A2 | 9/2014 |
| EP | 3000408 A2 | 3/2016 |
| EP | 3135225 A2 | 3/2017 |
| EP | 3158947 A1 | 4/2017 |
| EP | 3173029 A1 | 5/2017 |
| FR | 2828952 B1 | 12/2005 |
| JP | 5301166 B2 | 9/2013 |
| JP | 2014530653 A | 11/2014 |
| JP | 2016508792 A | 3/2016 |
| JP | 2016513570 A | 5/2016 |
| JP | 2017500146 A | 1/2017 |
| JP | 2017513564 A | 6/2017 |
| JP | 2017527396 A | 9/2017 |
| JP | 6411461 B2 | 10/2018 |
| JP | 2019141659 A | 8/2019 |
| SU | 405234 A1 | 9/1975 |
| SU | 886900 A1 | 12/1981 |
| SU | 1333319 A2 | 8/1987 |
| SU | 1442191 A1 | 12/1988 |
| SU | 1459659 A1 | 2/1989 |
| WO | WO-8602254 A1 | 4/1986 |
| WO | WO-9005489 A1 | 5/1990 |
| WO | WO-9734533 A1 | 9/1997 |
| WO | WO-03094743 A1 | 11/2003 |
| WO | WO-03094746 A1 | 11/2003 |
| WO | WO-03094747 A1 | 11/2003 |
| WO | WO-2012142872 A1 | 10/2012 |
| WO | WO-2014106275 A1 | 7/2014 |
| WO | WO-2017026141 A1 | 2/2017 |
| WO | WO-2017034803 A2 | 3/2017 |
| WO | WO-2017156070 A1 | 9/2017 |
| WO | WO-2017214243 A1 | 12/2017 |
| WO | WO-2018005750 A1 | 1/2018 |
| WO | WO-2018071497 A1 | 4/2018 |
| WO | WO-2018118402 A1 | 6/2018 |
| WO | WO-2020081960 A1 | 4/2020 |
| WO | WO-2020131692 A1 | 6/2020 |

OTHER PUBLICATIONS

International Preliminary Report on Patentability for Application No. PCT/US2019/017646, mailed on Aug. 27, 2020, 10 pages.
International Preliminary Report on Patentability for Application No. PCT/US2019/019501, mailed Sep. 3, 2020, 7 pages.
International Search Report and Written Opinion for Application No. PCT/US2020/025655, mailed Jul. 22, 2020, 8 pages.
International Search Report and Written Opinion for Application No. PCT/US19/17646, mailed on Apr. 16, 2019. 11 pages.

(56) References Cited

OTHER PUBLICATIONS

International Search Report and Written Opinion for Application No. PCT/US2019/019501, mailed May 9, 2019, 8 pages.
International Search Report and Written Opinion for Application No. PCT/US2019/056979, mailed Dec. 18, 2019, 8 pages.
International Search Report and Written Opinion for Application No. PCT/US2019/062344, mailed Mar. 23, 2020, 17 pages.
International Search Report and Written Opinion for Application No. PCT/US2019/062768, mailed Mar. 9, 2020, 15 pages.
International Search Report and Written Opinion for Application No. PCT/US2019/064861, mailed Mar. 30, 2020, 18 pages.
International Search Report and Written Opinion for Application No. PCT/US2019/066513, mailed Apr. 21, 2020, 8 pages.
International Search Report and Written Opinion for Application No. PCT/US2019/066530, mailed Apr. 21, 2020, 8 pages.
International Search Report and Written Opinion for Application No. PCT/US2020/020672, mailed Jun. 29, 2020, 10 pages.
International Search Report and Written Opinion for Application No. PCT/US2020/033481. mailed Sep. 3, 2020, 22 pages.
Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.
International Search Report and Written Opinion for Application No. PCT/US2021/065544 mailed Jun. 2, 2022, 21 pages.
International Search Report and Written Opinion for Application No. PCT/US2021/065308, mailed Apr. 21, 2022. 13 pages.
International Search Report and Written Opinion for Application No. PCT/US2021/012284, mailed May 6, 2021, 23 pages.
Supplementary European Search Report for Application No. EP19873128.3, mailed on Jun. 22, 2022, 7 pages.
European Search Report (Corrected version) for Application No. EP19750317.0, mailed on Mar. 28, 2022, 26 pages.
Partial European Search Report for Application No. EP19757451.0, mailed on Feb. 2, 2022, 12 pages.

\* cited by examiner

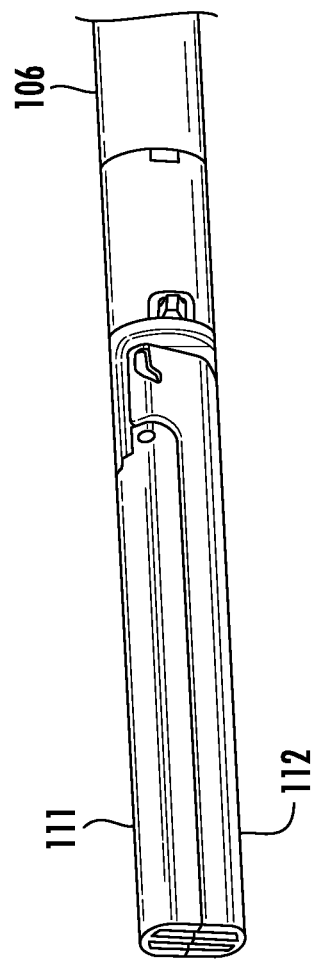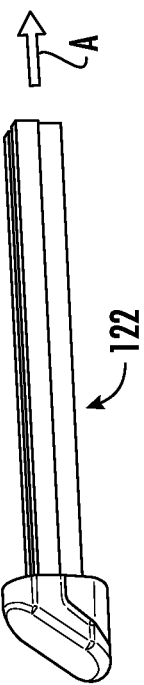
FIG. 2A

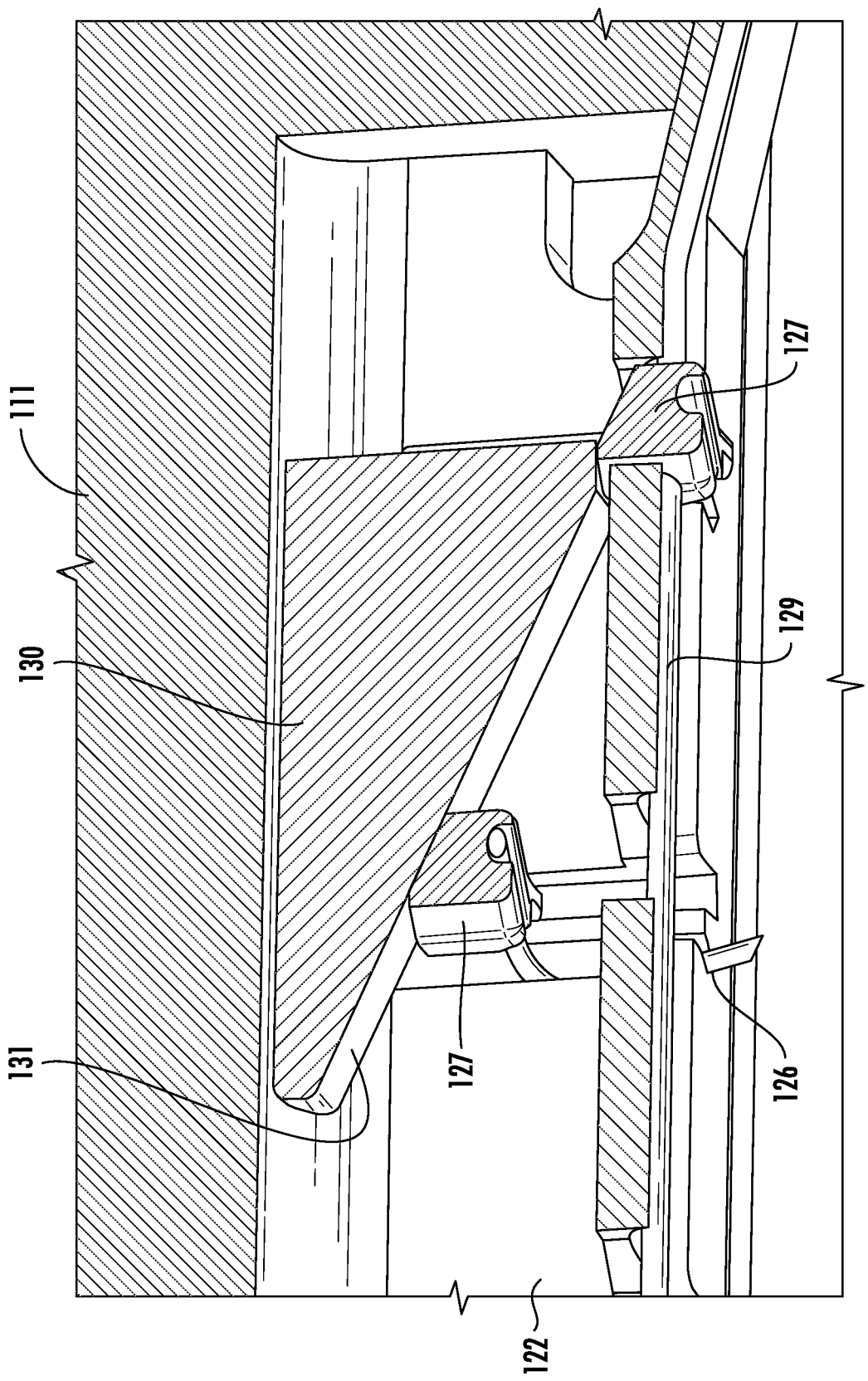

ENDOSCOPIC PURSE STRING SUTURE SURGICAL DEVICE

CROSS REFERENCE TO RELATED APPLICATIONS

This application is the National Stage of International Application No. PCT/US2019/056979 filed Oct. 18, 2019 which claims benefit of U.S. Provisional Application No. 62/747,912 filed Oct. 19, 2018, the entirety of each are herein incorporated by reference.

BACKGROUND

Surgical anastomosis joins together two hollow organs, usually to restore continuity after resection, or less commonly to bypass an unresectable disease process. Anastomosis is typically performed on blood vessels including arteries and veins; gastrointestinal tract including esophagus, stomach, small intestine, colon, rectum, anus, bile ducts and pancreas; or urinary tract including ureters, urinary bladder and urethra, and fallopian tubes.

Purse string sutures and purse string appliers may be used during anastomosis procedures. A suture is typically placed using a needle, staples or other suitable means for attaching the suture to the tissue. After attachment, the ends of the suture remain loose for pulling to contract or close the tissue.

In minimally invasive, e.g. endoscopic, surgical anastomosis procedures, it would be advantageous to provide an endoscopic purse string device which could apply purse string sutures in a minimally invasive manner and that is compatible with a robotic surgical system.

SUMMARY

The following presents a simplified summary of the claimed subject matter in order to provide a basic understanding of some aspects of the claimed subject matter. This summary is not an extensive overview of the claimed subject matter. It is intended to neither identify key or critical elements of the claimed subject matter nor delineate the scope of the claimed subject matter. Its sole purpose is to present some concepts of the claimed subject matter in a simplified form as a prelude to the more detailed description that is presented later.

The present disclosure relates to surgical staplers for applying a suture to tissue having a cartridge including a shuttle configured to engage a series of staple drivers for ejecting staples upon distal translation of a drive member.

In another aspect, the present disclosure relates to surgical staplers for applying a suture to tissue including a cartridge having a first upper portion and a second lower portion connected by a connecting member and configured to be installed along the longitudinal axis of the end effector.

In another aspect, the present disclosure relates to a jaw-closing mechanism having a first and second link member secured to a first and second jaw, the first and second links coupled with a first and second pair of drive cables configured to apply force to the first and second link members to cause them to rotate about pivot pins and ride through a cam slot having a proximal portion for parallel closure of the jaws and a distal portion for angular closure of the jaws.

In embodiments, a surgical stapler for applying a suture to tissue in accordance with this disclosure includes an elongated shaft having a distal end and a proximal end. The end effector defines a longitudinal axis and includes a first jaw and a second jaw. The first jaw and second jaw are configured to receive a cartridge and to move from an open position to a closed position to apply staples to tissue such that a suture, in combination with the staples, form a purse string with the tissue when the stapler is activated. The surgical stapler further includes a drive member configured to translate distally and retract proximally through the end effector, and an actuation mechanism configured to translate the drive member distally through the end effector and retract the drive member proximally through the end effector. The cartridge includes a first upper portion configured to fit into the first jaw and a second lower portion configured to fit into the second jaw. The cartridge further includes a shuttle configured to engage a series of staple drivers for ejecting staples upon distal translation of the drive member In embodiments, the first upper portion and second lower portion are connected by a connecting member, and the cartridge is configured to be installed along the longitudinal axis of the end effector.

In another aspect, a jaw-closing mechanism for a surgical stapler for applying suture to tissue in accordance with this disclosure relates to a first link member and a second link member. The first and second link members are configured to rotate about a pair of pivot pins upon application of force to the first and second link members. A pair of outer pins are configured to secure the first and second link members to a first jaw and a second jaw. A first and second pair of drive cables are configured to apply force to the first and second links to cause rotation about the pivot pins. The jaw-closing mechanism further includes a cam slot formed on one of the jaws configured to accept a cam slot pin of at least one of the link members. The cam slot has a proximal portion for parallel closure of the jaws, and a distal portion for angular closure of the jaws.

BRIEF DESCRIPTION OF THE DRAWINGS

The above and other aspects, features, and advantages of the present surgical instruments will become more apparent in light of the following detailed description when taken in conjunction with the accompanying drawings in which:

FIG. 2A is a perspective view showing installation of a cartridge into the surgical instrument of FIG. 1;

FIG. 13 is a partial perspective view with parts removed of a partially driven shuttle contacting a staple driver as it moves distally upon actuation;

DETAILED DESCRIPTION

Particular embodiments of the present surgical instruments are described hereinbelow with reference to the accompanying drawings; however, it is to be understood that the disclosed embodiments are merely exemplary of the disclosure and may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure. Well-known functions or constructions are not described in detail to avoid obscuring the present disclosure in any unnecessary detail.

While the following disclosure is presented with respect to a surgical instrument for forming purse strings, it should be understood that certain features of the presently described surgical instruments may be readily adapted for use in any type of surgical clamping, cutting, or sealing instruments. The surgical clamping and cutting instrument may be a minimally invasive (e.g., laparoscopic) instrument or an instrument used for open surgery.

Additionally, the features of the presently described surgical stapling instruments may be readily adapted for use in surgical instruments that are activated using any technique within the purview of those skilled in the art, such as, for example, manually activated surgical instruments, powered surgical instruments (e.g., electro-mechanically powered instruments), robotic surgical instruments, and the like.

Figure 1:
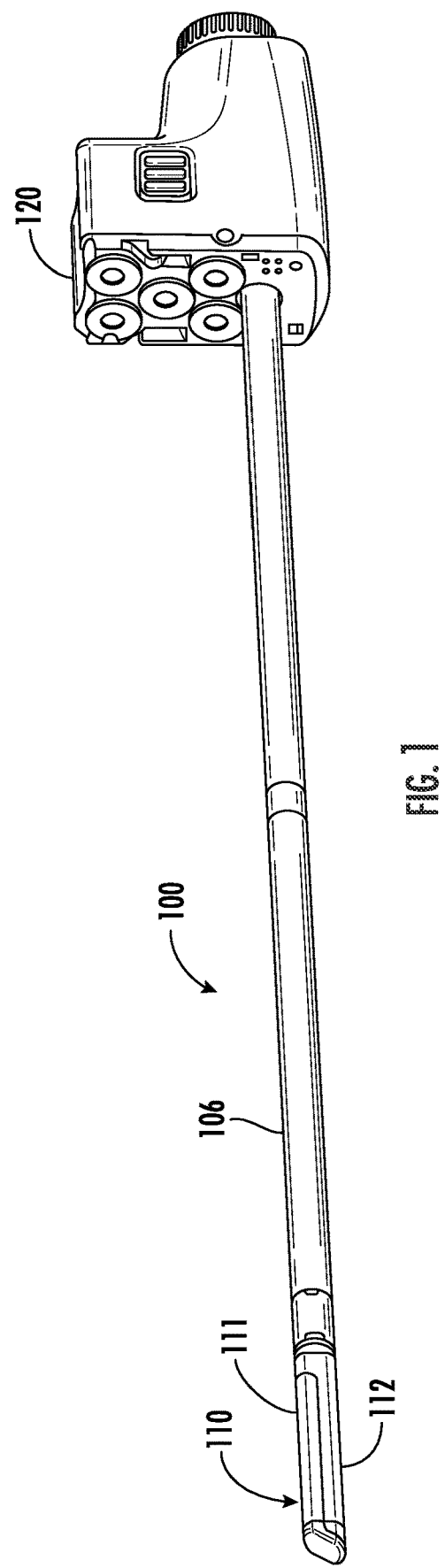
FIG. 1 is a perspective view of an illustrative surgical instrument in accordance with the present disclosure.

FIG. 1 is a perspective view of an illustrative surgical instrument 100 in accordance with embodiments of the present disclosure having a backend mechanism 120, and an end effector 110 mounted on an elongated shaft 106. Backend mechanism 120 typically provides a mechanical coupling between the drive tendons or cables of the instrument and motorized axes of the mechanical interface of a drive system. Further details of known backend mechanisms and surgical systems are described, for example, in U.S. Pat. Nos. 8,597,280, 7,048,745, and 10,016,244. Each of these patents is hereby incorporated by reference in its entirety.

Actuation mechanisms of surgical instrument 100 employ drive cables that are used in conjunction with a system of motors and pulleys. Powered surgical systems, including robotic surgical systems that utilize drive cables connected to a system of motors and pulleys for various functions including opening and closing of jaws, as well as for movement and actuation of end effectors are well known. Further details of known drive cable surgical systems are described, for example, in U.S. Pat. Nos. 7,666,191 and 9,050,119 both of which are hereby incorporated by reference in their entireties.

Figure 1A:
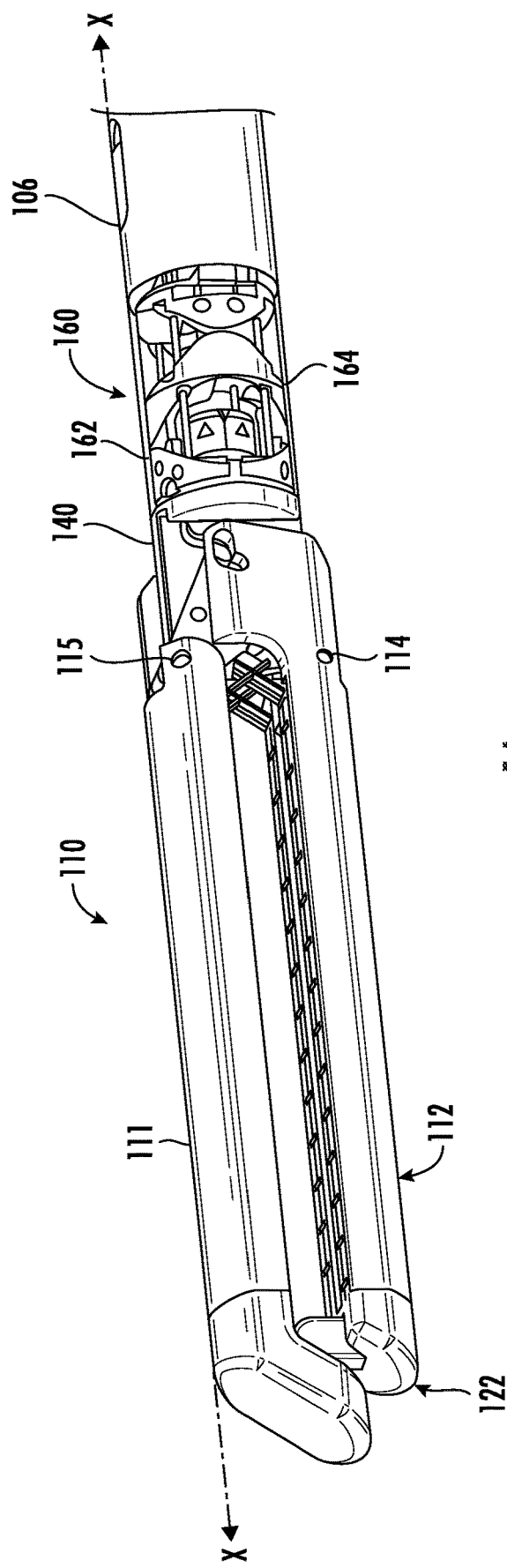
FIG. 1A is a perspective view of the distal end portion of the surgical instrument of FIG. 1 shown having an end effector mounted to an elongated shaft and a backend mechanism configured to actuate the instrument.

FIG. 1A shows the distal end portion of surgical instrument 100, including an end effector 110 defining a longitudinal axis X-X and having a first jaw 111, a second jaw 112, a cartridge 122, a clevis 140 for mounting jaws 111, 112 to the instrument, and an articulation mechanism, such as wrist 160. First and second jaws 111, 112 are configured to move from an open position to a closed position. In the closed position, jaws 111, 112 cooperate to clamp tissue.

Figure 2:
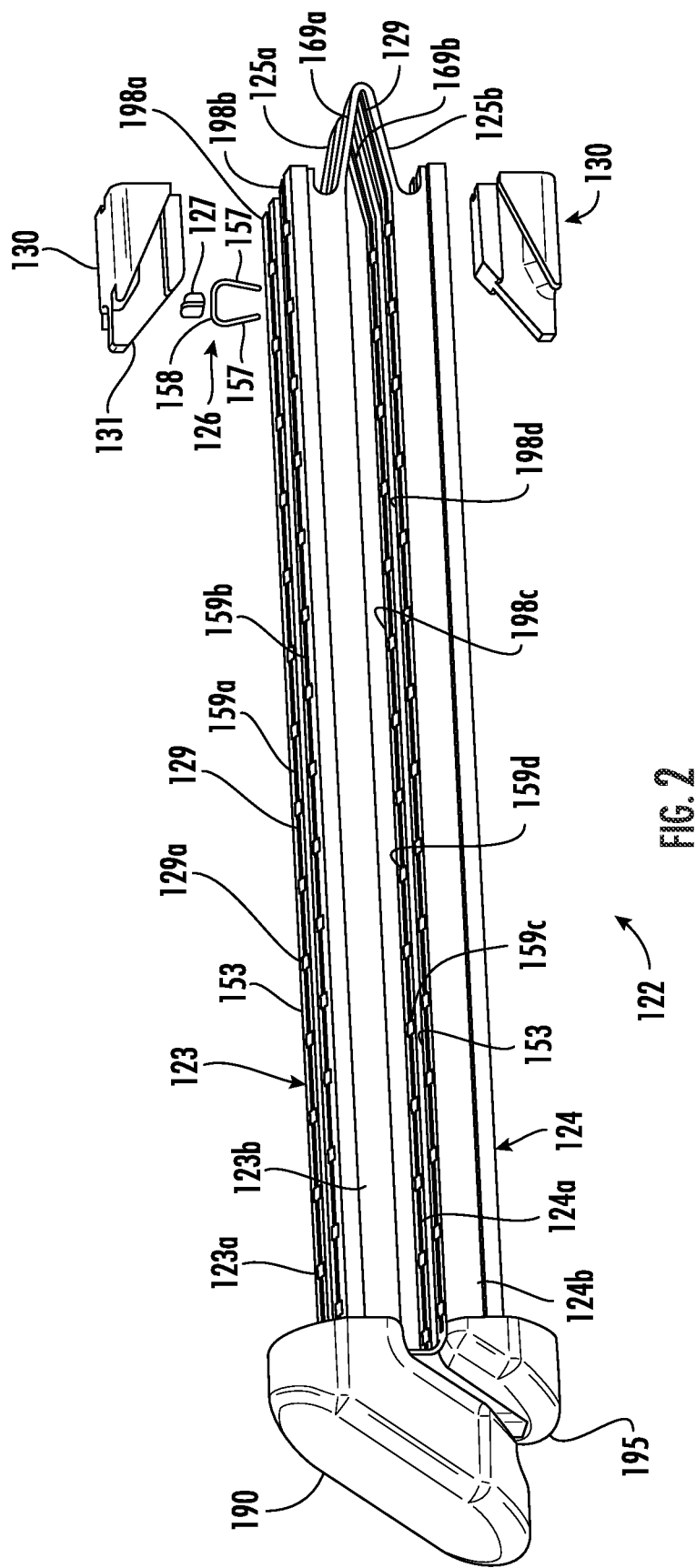
FIG. 2 is a perspective exploded view of a staple cartridge suitable for use with the surgical instrument of FIG. 1.
Figure 2B:
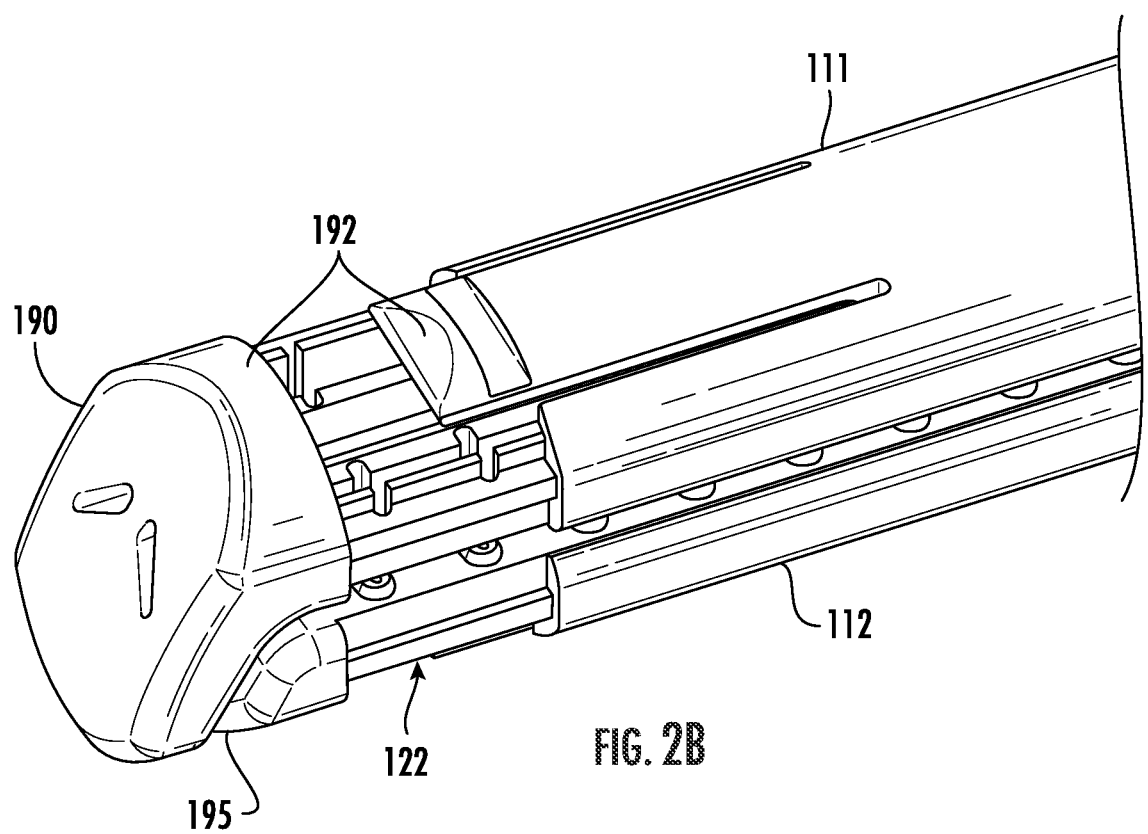
FIG. 2B illustrates a portion of an illustrative surgical instrument in accordance with this disclosure having a flexing latch.

FIG. 2 depicts cartridge 122. In embodiments, cartridge 122 includes an upper portion 123 having a first and second side 123a, 123b, and a lower portion 124 having a first and second side 124a, 124b. Each pair of first and second sides 123a, 123b and 124a, 124b is separated by a center knife channel 153. Each side 123a, 123b and 124a, 124b defines a tissue contacting surface 198a, 198b and 198c, 198d having staple retaining pockets 128 and a suture retaining channel 159a-d formed therein. (See also FIG. 3.) In embodiments, tissue contacting surfaces 198a-d may further include protrusions (not shown) positioned about staple receiving pockets 128. Protrusions help to further secure clamped tissue and to resist movement that might be induced from forces created by the severing and stapling of clamped tissue. Staples 126 are supported on corresponding staple drivers 127 provided within respective staple receiving pockets 128 formed in cartridge 122. Staple receiving pockets 128 may be cutouts that are substantially perpendicular to the longitudinal axis of end effector 110, and similar in length to the desired size of staples 126 to be fired. Each staple 126 include legs 157 and a backspan 158. Suture retaining channels 159a-d run substantially parallel to the longitudinal axis of end effector 110 and are substantially aligned with the center of staple receiving pockets 128 so that upon firing of staples 126, sutures 129a, 129b are captured at various locations between staples 126 and tissue 197 as described in more detail below.

Upper portion 123 and lower portion 124 of cartridge 122 are configured to be contained within first jaw 111 and second jaw 112, respectively. Side 123a of upper portion 123 is connected to side 124a of lower portion 124 at the proximal end of cartridge 122 by living hinge 125a. Likewise, side 123b of upper portion 123 is connected to side 124b of lower portion 124 at the proximal end of cartridge 122 by living hinge 125b. Channels 159a, 159c of sides 123a and 124a of cartridge 122 extend to living hinge 125a and align with living hinge channel 169a. Likewise, channels 159b, 159d of sides 123b and 124b of cartridge 122 extend to living hinge 125b and align with living hinge channel 169b. In this manner, sutures 129a, 129b may be guided from lower portion 124 to upper portion 123 on each side of the instrument to form a loop upon clamping of tissue and actuation of the surgical instrument.

Cartridge 122 also may include a shuttle 130 having an inclined distal portion 131 that, upon distal movement, sequentially acts on staple drivers 127, camming them towards grasped tissue thereby forcing the staples towards grasped tissue. Legs 157 of staples 126 are positioned on either side of sutures 129a, 129b, and are configured to secure sutures 129a, 129b to grasped tissue upon actuation of the surgical instrument. Details of the mechanism for formation of staples 126 to provide purse strings are described below. (See FIGS. 13 and 13A.)

Figure 2C:
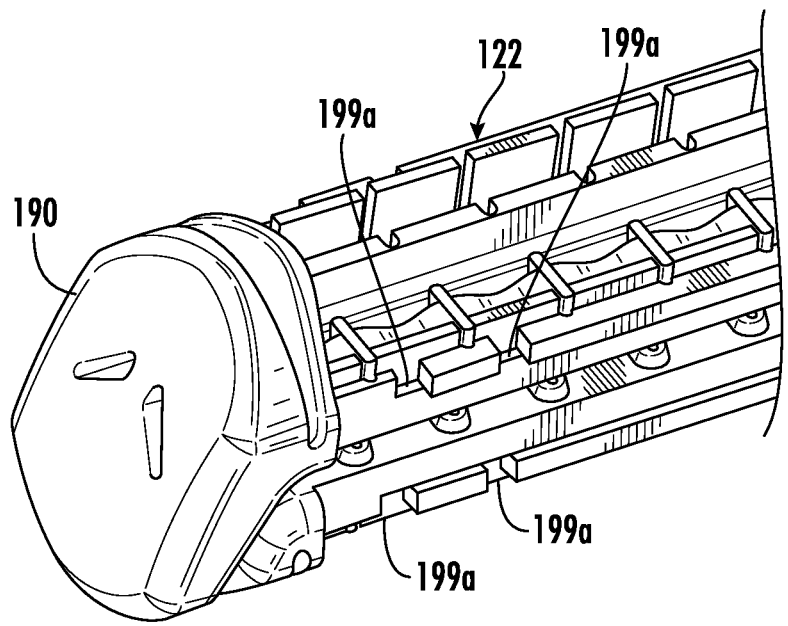
FIG. 2C illustrates a portion of an illustrative cartridge suitable for use with the surgical instrument of FIG. 1.
Figure 2D:
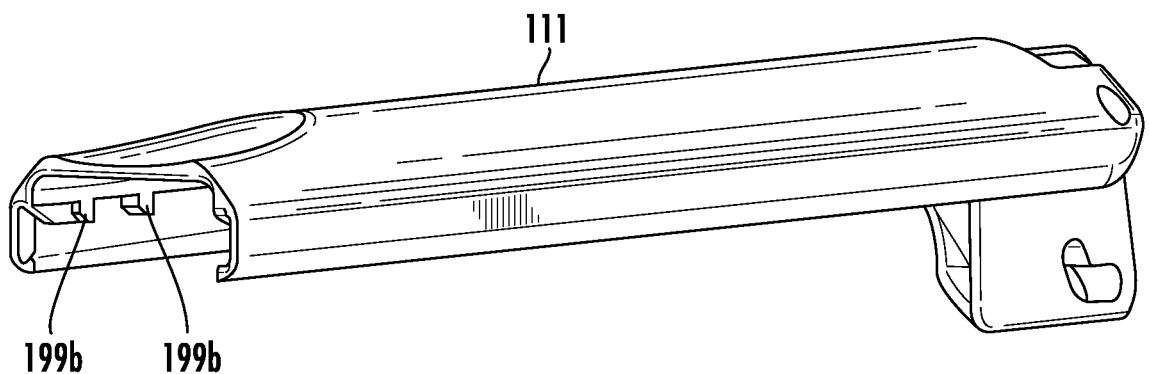
FIG. 2D illustrates an illustrative jaw suitable for use with the surgical instrument of FIG. 1 having hooks configured to engage and retain the cartridge of FIG. 2C within the jaws.

In embodiments, upper portion 123 of cartridge 122 includes distal end portion 190 that, upon closing of jaws 111, 112, overlaps a distal end portion 195 of lower portion 124. Distal end portion 190 prevents cartridge 122 from sliding out of the jaws after installation. Distal end portion 190 may include a flexing latch member 192, that upon installation of cartridge 122 in jaws 111, 112 would engage with a recess (not shown) contained within jaw 111, retaining latch member 192 in place until defeated by application of finger pressure to release it. Flexure would provide an over-center snap feeling between the latched and the unlatched position, such that a surgeon would be able to feel the difference between the latched and unlatched positions. It is envisioned that latch 192 may be held in place by any number of desired mating features, such as a protrusion, or a cutout formed on jaw 111. In an alternative embodiment shown in FIGS. 2C-2D cartridge 122 may further include cutouts 199a configured to engage at least one hook 199b contained within jaws 111, 112. Upon installation, cartridge 122 may slightly pivot such that hooks 199b catch within recesses 199a helping to retain the cartridge 122 in place.

Figure 2E:
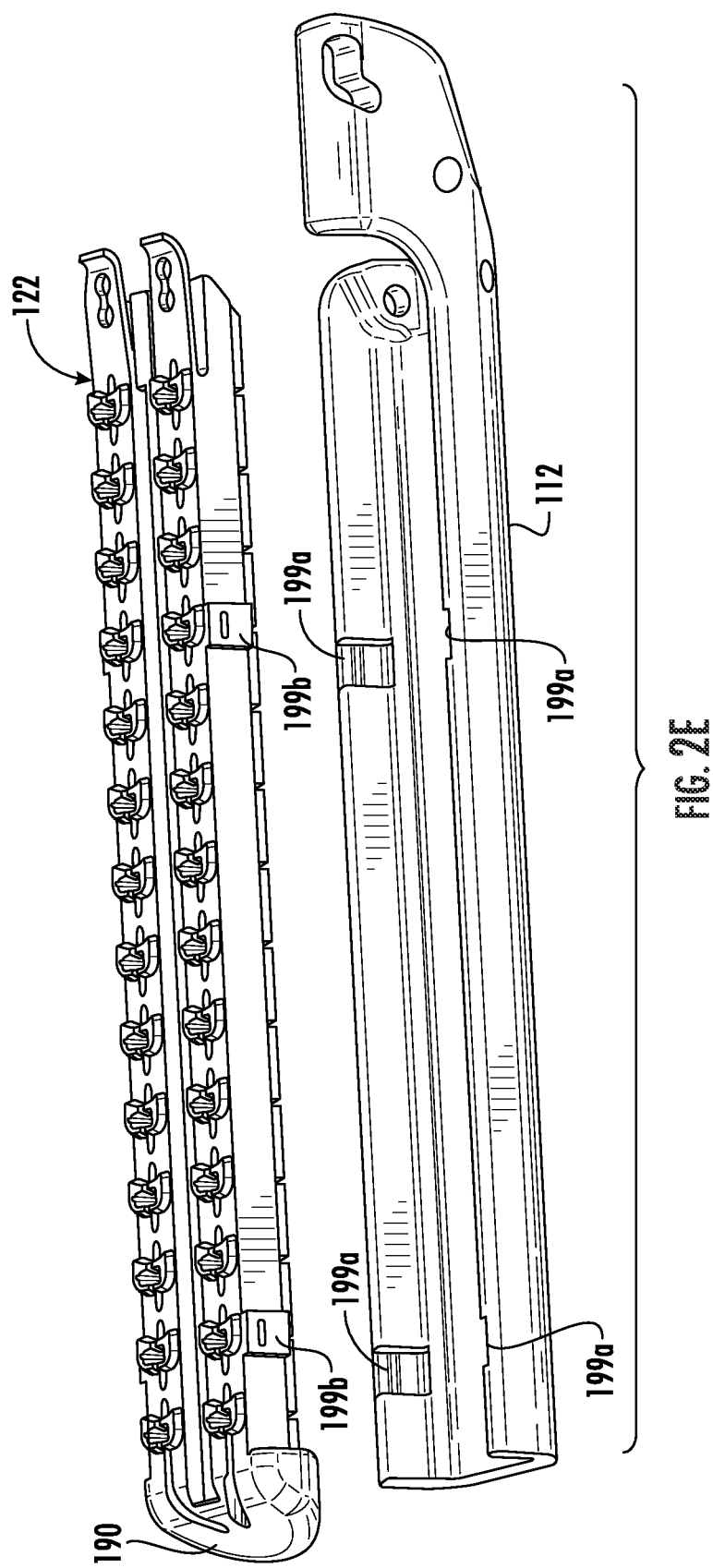
FIG. 2E illustrates an exploded view of another illustrative jaw and cartridge suitable for use with the surgical instrument of FIG. 1.

Distal end portions 129c of suture 129a extend beyond the distal ends of suture retaining slots 159a and 159c and distal end portions 129d of suture 129b extend beyond the distal ends of suture retaining slots 159b and 159d. Thus, suture 129a may, for example, extend from distal end portion 190, extending proximally in channel 159a within side 123a of upper portion 123 of cartridge 122, around living hinge 125a through living hinge channel 169a, and then extend distally along suture channel 159c of side 124a of lower portion 124 of cartridge 122. Cartridge 122 is installed in a direction substantially parallel to the longitudinal axis of end effector 110, and is inserted in the direction of arrow A from the distal end of surgical instrument 100 towards the proximal end of surgical instrument 100, as shown in FIG. 2A. In alternative embodiments, it is envisioned that the stapler may allow for installation of cartridge 122 in a radial direction that is substantially orthogonal to the longitudinal axis of end effector 110. FIG. 2E shows an illustrative jaw 112 configured to allow for radial installation of cartridge 122. Hooks 199b on the cartridge may engage recesses 199a formed on jaw 112 to help retain cartridge 122 within jaw 111 in a similar manner as previously described embodiments.

Figure 3:
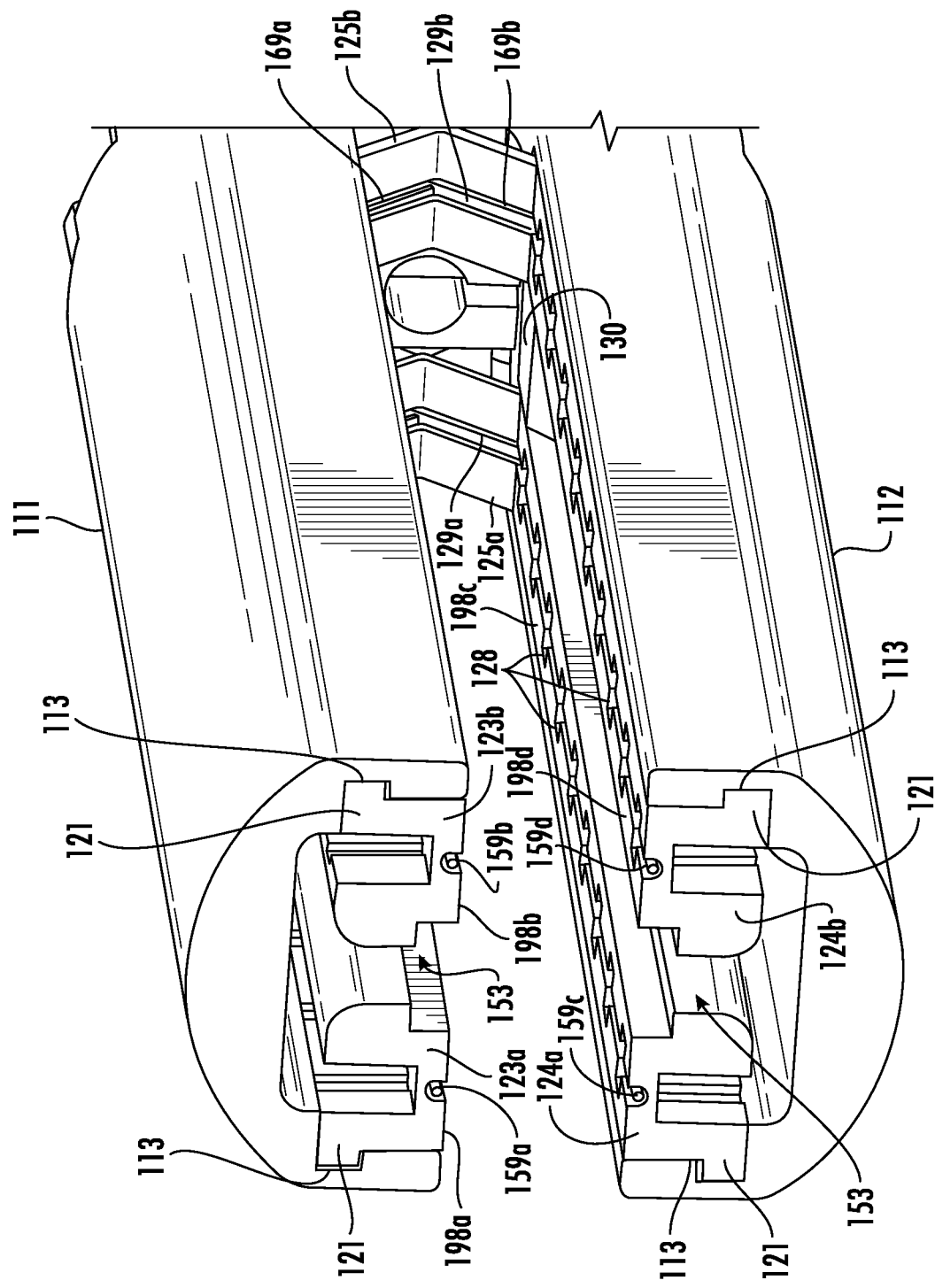
FIG. 3 is a partial perspective view of a portion of the end effector with a fresh reload installed.

As seen in FIG. 3, when a fresh unfired cartridge 122 is installed, shuttle 130 prevents unwanted separation of sides 123a and 123b of upper portion 123 of cartridge 122 and of sides 124a and 124b of lower portion 124 of cartridge 122. Additionally, cartridge 122 includes protrusions 121 configured to slide into slots 113 formed on jaws 111, 112. Slots 113 of jaws 111, 112 serve as guide rails for protrusions 121 to ensure proper alignment upon installation of a fresh cartridge 122. Additionally, the interaction of cartridge protrusions 121 and slots 113 limits upward and downward movement of cartridge 122 during installation and firing.

Figure 4:
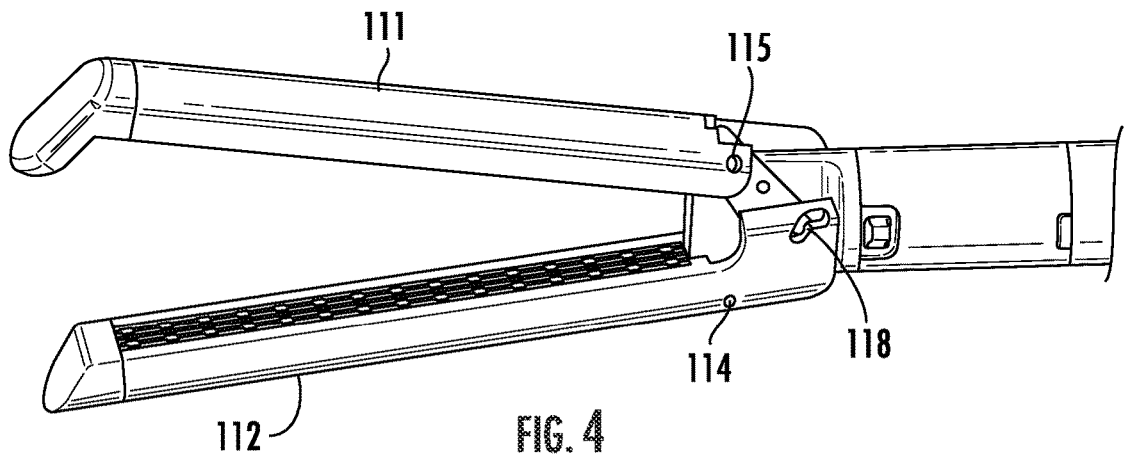
FIG. 4 is a perspective view of the distal end portion of the surgical instrument of FIG. 1 with the jaws in the angled open position.
Figure 5:
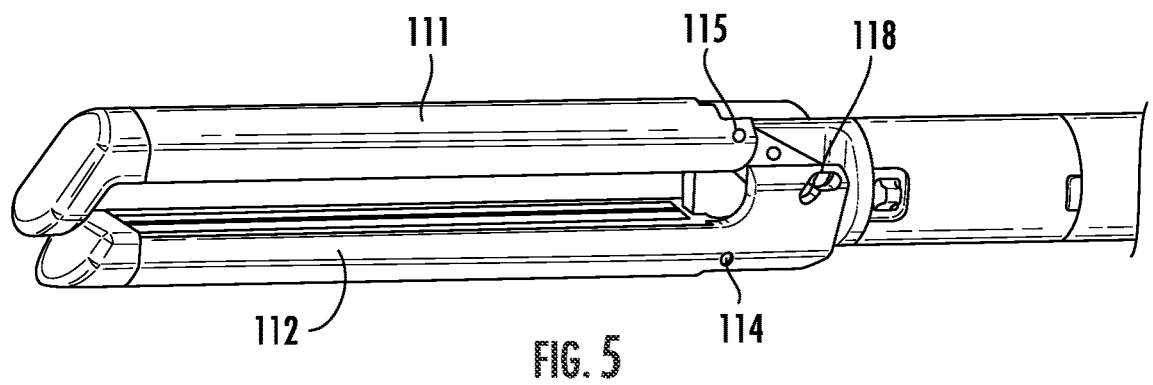
FIG. 5 is a perspective view of the distal end portion of the surgical instrument of FIG. 1 with the jaws in the parallel position.
Figure 6:
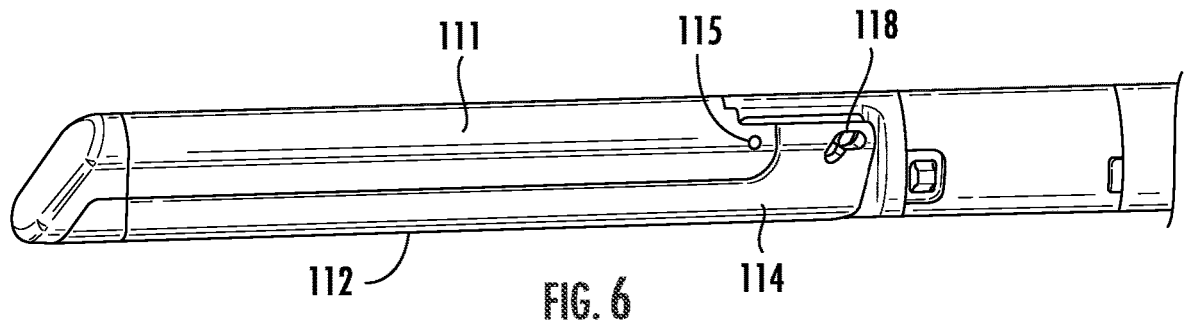
FIG. 6 is a perspective view of the distal end portion of the surgical instrument of FIG. 1 with the jaws in the completely closed position.

FIGS. 4-6 depict the movement of jaws 111, 112 as the instrument is closed in preparation for actuation.

In FIG. 4, jaws 111, 112 are in an open position, resembling a grasper, and are in an angled-closure zone. Jaws 111, 112 close angularly until they are substantially parallel, as shown in FIG. 5. Once jaws 111, 112 are substantially parallel they continue to close while remaining substantially parallel to compress tissue. Once closed about tissue, the instrument may be fired to cut and insert staples into the grasped tissue, while causing sutures 129a, 129b to be captured by the staples form a purse string around the clamped tissue. The mechanism by which the jaws are opened and closed are described in more detail below.

Figure 7:
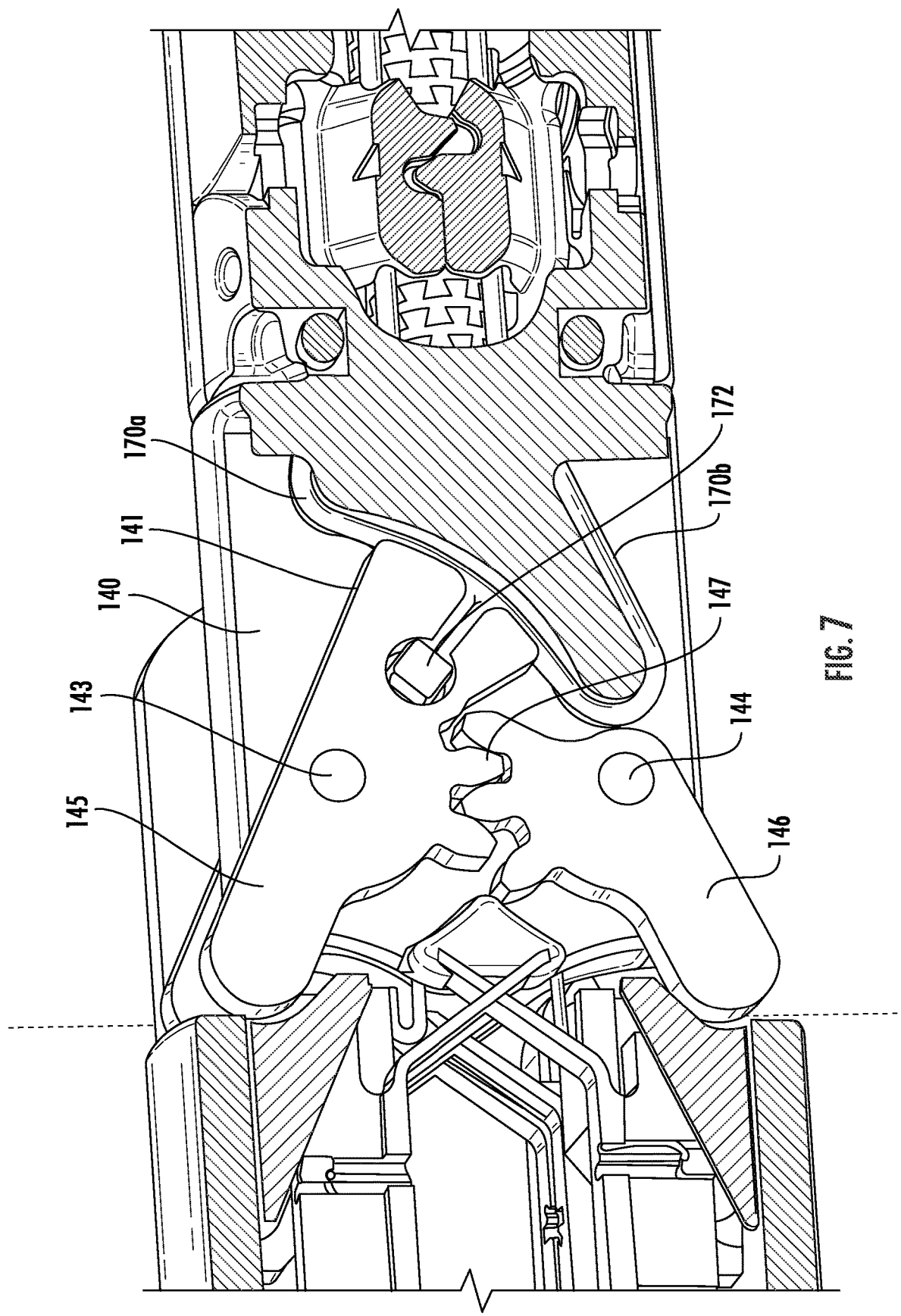
FIG. 7 is a cross-sectional perspective view of the jaw closure mechanism of the surgical instrument of FIG. 1.

FIG. 7 shows a portion of surgical instrument 100 configured to open and close the jaws including clevis 140, first link member 145, second link member 146, and drive cables 170a, 170b.

As shown in FIG. 7, two drive cables 170a, 170b route symmetrically to the backend of surgical instrument 100, and terminate in a knot 172 within the proximal end 141 of a first link member 145. As cables 170a, 170b are pulled by the force of the motor (not shown) or via some other mechanism, first link member 145 rotates about pivot pin 143 on clevis 140, causing a second link member 146 to rotate about pivot pin 144 on clevis 140, thereby moving the jaws towards an open or closed position depending on which drive cable was pulled. The resulting jaw force is substantially similar to the cable pull force. One of ordinary skill will appreciate that a pair of drive cables may be present on each side, of surgical instrument 100, each pair of drive cables including a first cable for closing a first link, and a second cable for opening the first link. Using four cables in total for opening and closing of the jaw reduces the stress on each cable, and allows for symmetrically balanced cable forces through the wrist 160 such that actuating the jaw does not impart pitch or yaw forces into the wrist. (See FIG. 10.)

Figure 8:
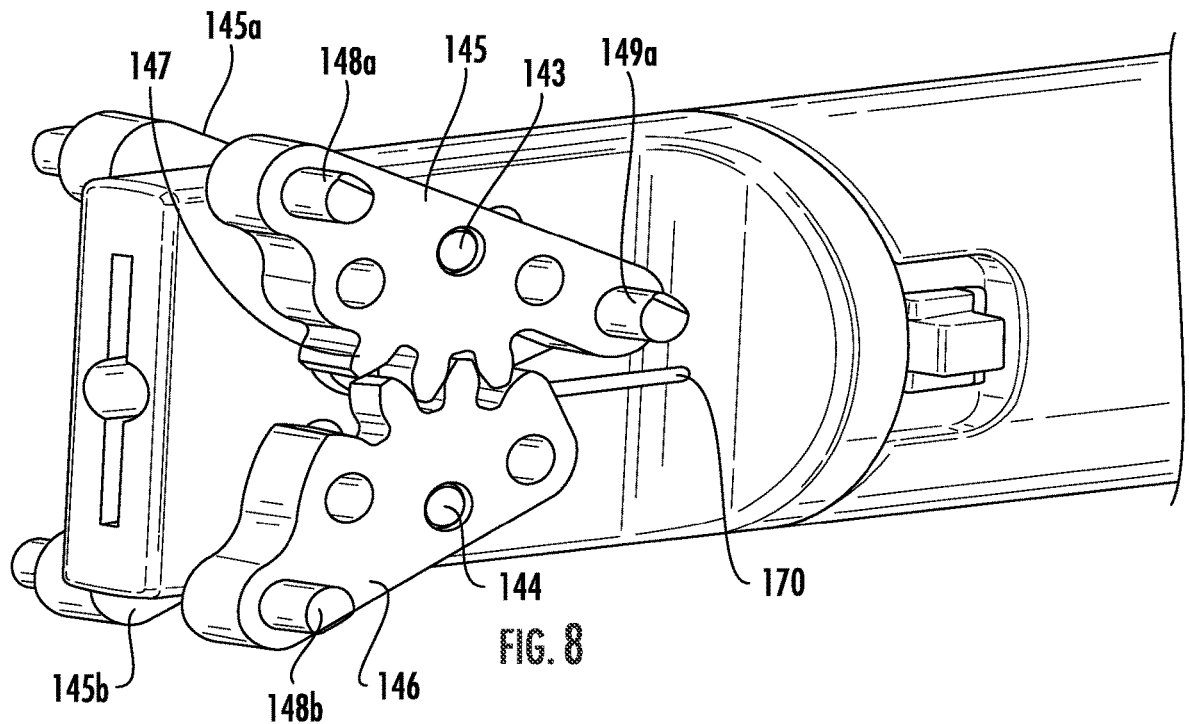
FIG. 8 is a perspective view of the first and second links of the jaw closure mechanism.
Figure 9:
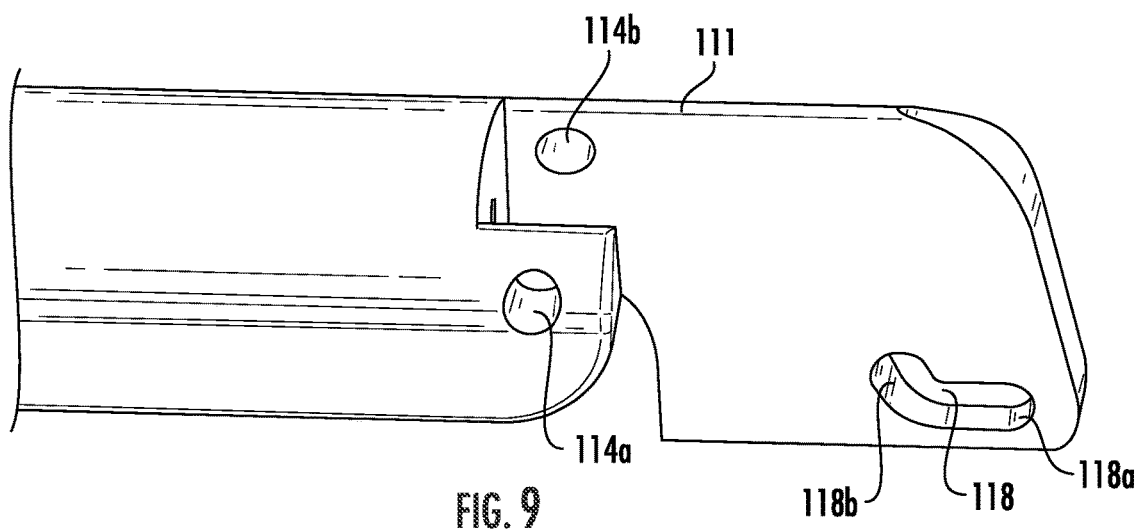
FIG. 9 is a perspective view of a portion of a jaw of the surgical instrument of FIG. 1.

As illustrated in FIGS. 8 and 9, link member 145 includes upper outer pin 148a, and link member 146 includes lower outer pin 148b. Upper outer pin 148a is configured to be positioned within opening 114 of jaw 111, while lower outer pin 148b is configured to be positioned within an opening 115 of jaw 112. (See, e.g., FIGS. 1A and 4-6.) Link member 145 also include cam slot pin 149a configured to engage and ride within cam slot 118 formed on jaw 111. Cam slot 118 is designed such that the proximal portion 118a of cam slot 118 allows for parallel closure of jaw 111, while the distal portion 118b of cam slot 118 allows for angular closure of jaws 111 upon rotation of link members 145, 146 due to the force of drive cables 170a, 170b upon actuation of the surgical instrument. A second set of link members 145a, 145b and corresponding openings and cam slot, similar to link members 145, 146 is present on the far side of clevis 140 jaws 111, 112 and function similarly to link members 145, 146. Links members 145, 146 also include gear teeth 147 to enforce equally symmetric motion of jaws 111,112.

Figure 10:
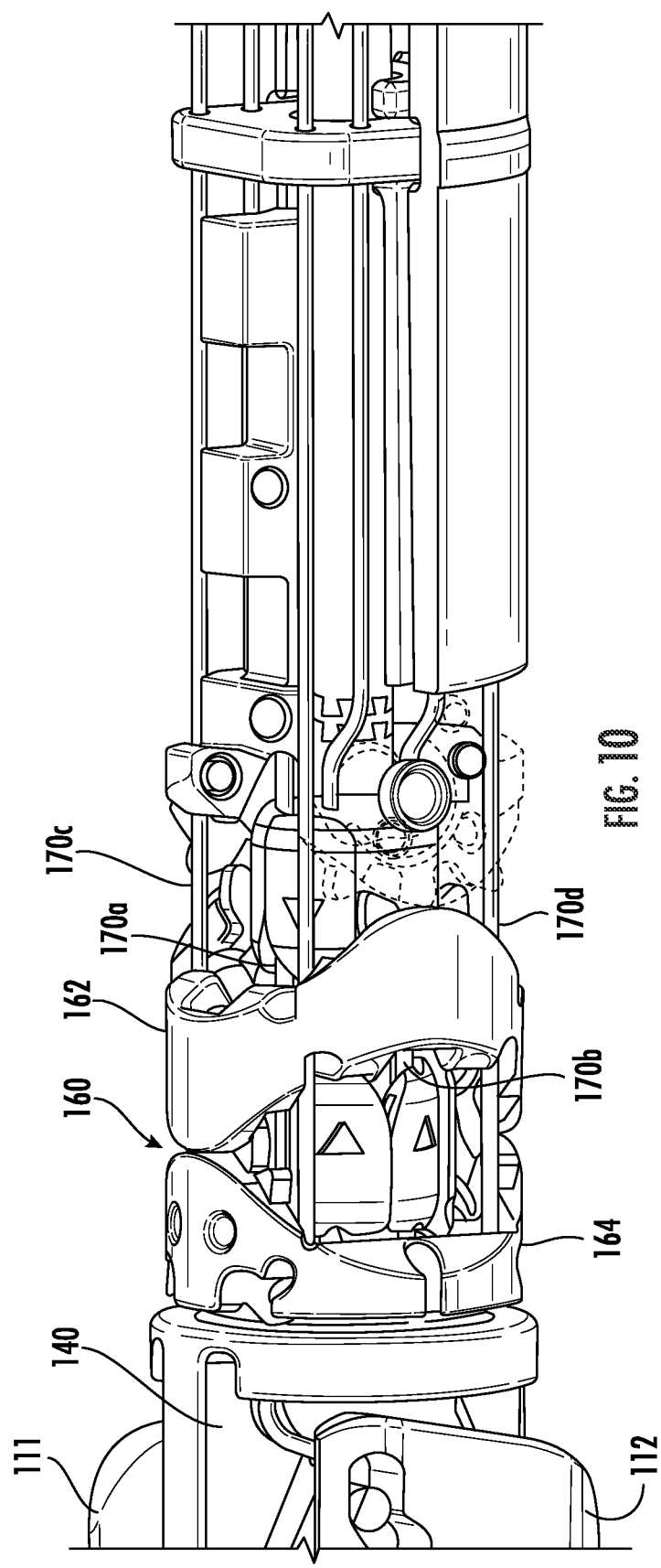
FIG. 10 is a perspective view of the articulation mechanism of the surgical instrument of FIG. 1 with parts removed to reveal internal structures.

FIG. 10 illustrates the articulation mechanism including an articulating wrist 160, and drive cables 170c, 170d running from the proximal end of the instrument to wrist links 162, 164. Wrist 160 includes a number of links that provide a desired amount of motion, such as +/−90 degrees in a pitch or yaw direction. In embodiments, a single joint can provide up to a 90 degree angular deflection. According to an exemplary embodiment, a wrist may include a plurality of links to achieve higher ranges of motion, such as, for example, wrists having a range of motion of up to +/−180 degrees in a pitch or yaw direction. Typically, actuation elements such as, for example, pull/pull tendons or push/pull rods, and electrical conductors that are connected to a wrist and/or end effector of an instrument may extend through the elongated shaft of the instrument. Further, the actuation elements may extend through the elongated shaft and connect to a transmission mechanism that typically provides a mechanical coupling of the drive tendons to drive motors. As noted above, surgical instrument 100 may include two pairs of drive cables for opening and closing of the jaws, reducing the stress on each cable, and allowing for symmetrically balanced cable forces through wrist 160 such that actuating the jaw does not impart pitch or yaw forces into the wrist. Additionally, it is envisioned that the cables may merge within the mid-section of surgical instrument 100 such that only two cables are presented at the input capstans (not shown). This type of merging allows for a pulley to maintain cable length conservation as the wrist pitches or yaws. Additional details of other joints and wrist actuation elements usable with the embodiments disclosed herein, are disclosed in Int'l. Pub. No. WO 2015/127250A1, the entire disclosure of which is incorporated by reference herein.

Figure 11:
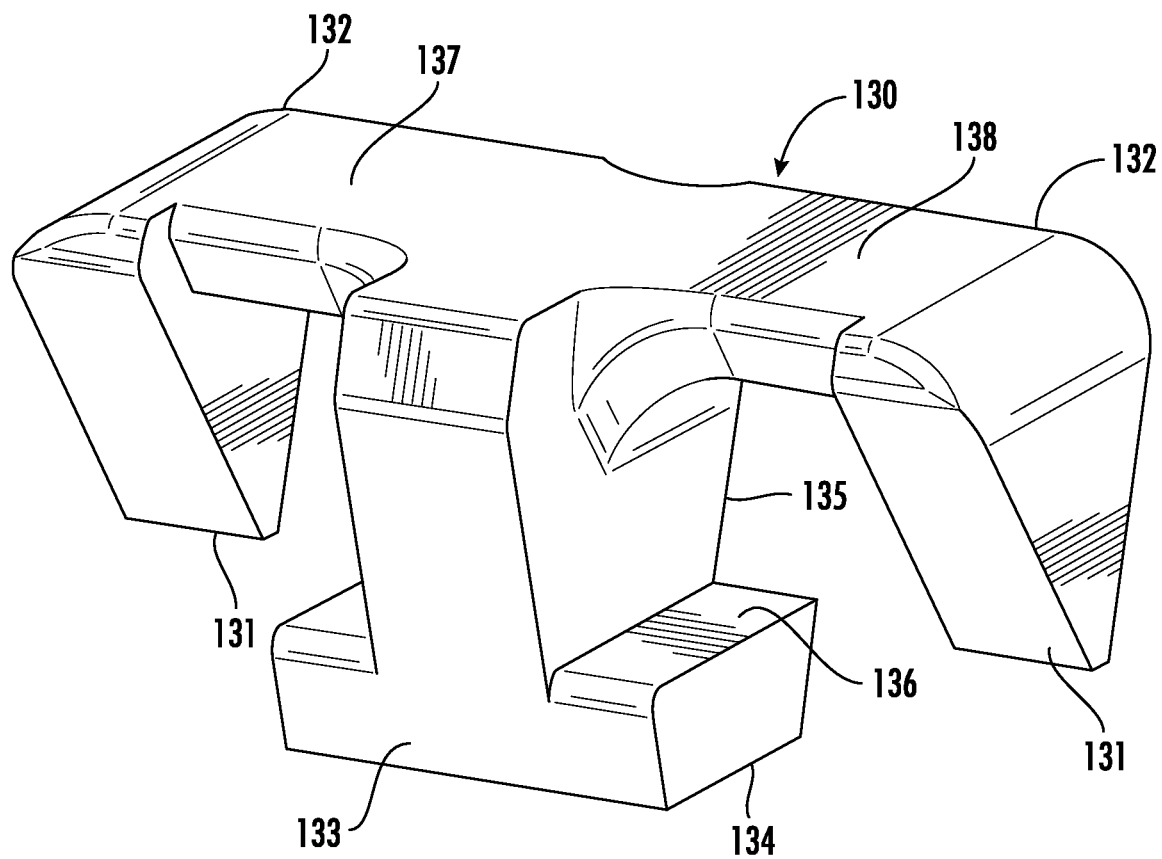
FIG. 11 is a perspective view of the shuttle of the surgical instrument of FIG. 1.
Figure 11A:
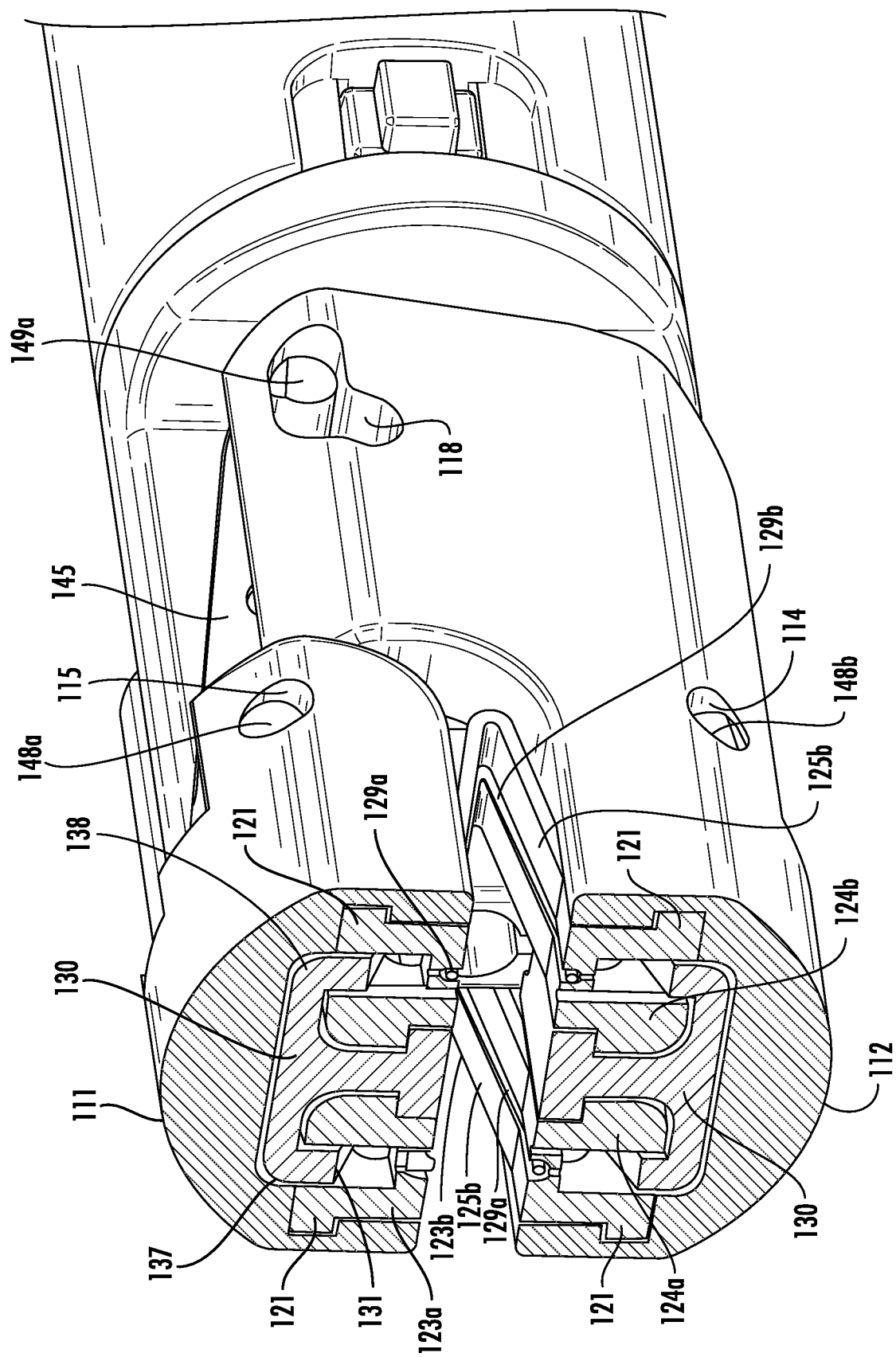
FIG. 11A is a partial perspective view with parts removed showing an unfired cartridge installed in the surgical instrument of FIG. 1.

FIGS. 11 and 11A show shuttles 130 contained in cartridge 122. Each shuttle 130 has a body 135 including inclined distal portions 131 and wings 137, 138. A shuttle 130 is positioned in each of upper and lower portions 123, 124 of cartridge 122 and prevent first side 123a and second side 123b of upper portion 123 and first side 124a and second side 124b of lower portion 124 from splaying during handling to ensure that cartridge 122 fits within slots 113 of jaws 111, 112. (See FIG. 11A.) Upon distal movement of shuttle 130, inclined distal portions 131 sequentially act on staple drivers 127, camming them upwardly thereby forcing staples 126 through staple receiving pockets 128. Shuttle 130 also includes proximal faces 132 that may be substantially perpendicular to the axis of end effector 110. Leading edge 133 of shuttle 130 herds tissue toward the center knife channel 153 so that the tissue may be severed by knife 151. (See FIG. 13.) Shuttle 130 also includes inner edge 134 which is described in further detail below. (See FIG. 15.)

Figure 12:
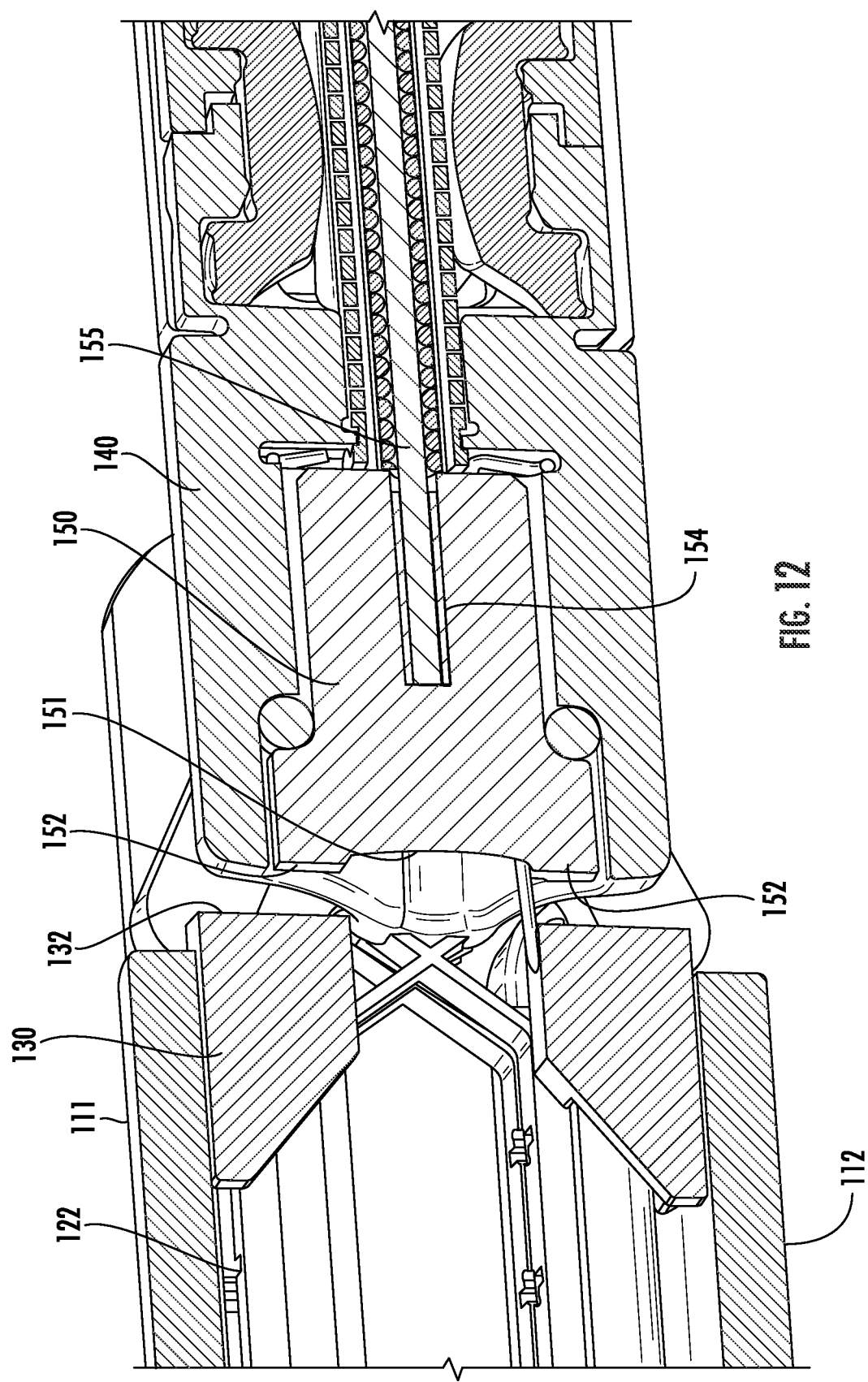
FIG. 12 is a cross-sectional perspective view of the drive mechanism of the surgical instrument of FIG. 1 with parts removed showing a drive member configured to drive distally upon actuation.

FIGS. 12-13 illustrate distal translation of the components of surgical instrument 100 upon actuation to sever and insert staples into clamped tissue such that a purse string is formed by sutures 129a, 129b.

FIG. 12 shows a drive member 150 having an integrated knife edge 151, shuttles 130, clevis 140, and drive rod 155. Upon actuation of surgical instrument 100, drive member 150 is pushed distally or pulled proximally through center knife channel 153 of cartridge 122 by drive rod 155 that is secured to a proximal cutout 154 formed on drive member 150. Drive member 150 may be coupled to any known actuation mechanisms including manually-activated actuators, motor-driven or powered actuators, or other types of actuation mechanisms. Drive member 150 includes distal edges 152 that are substantially aligned with proximal faces 132 of shuttle 130. Upon actuation of surgical instrument 100, distal edges 152 of drive member 150 engage proximal faces 132 of shuttle 130 translating shuttle 130 distally. Drive member 150 also includes knife edge 151 positioned between distal edges 152 for severing clamped tissue upon distal translation of drive member 150 through center knife channel 153 during firing of surgical instrument 100. The central position of knife channel 153 ensures that knife edge 151 severs tissue that is adjacent to and between the two portions of tissue that are stapled and sutured. (See FIG. 14.)

Figure 13A:
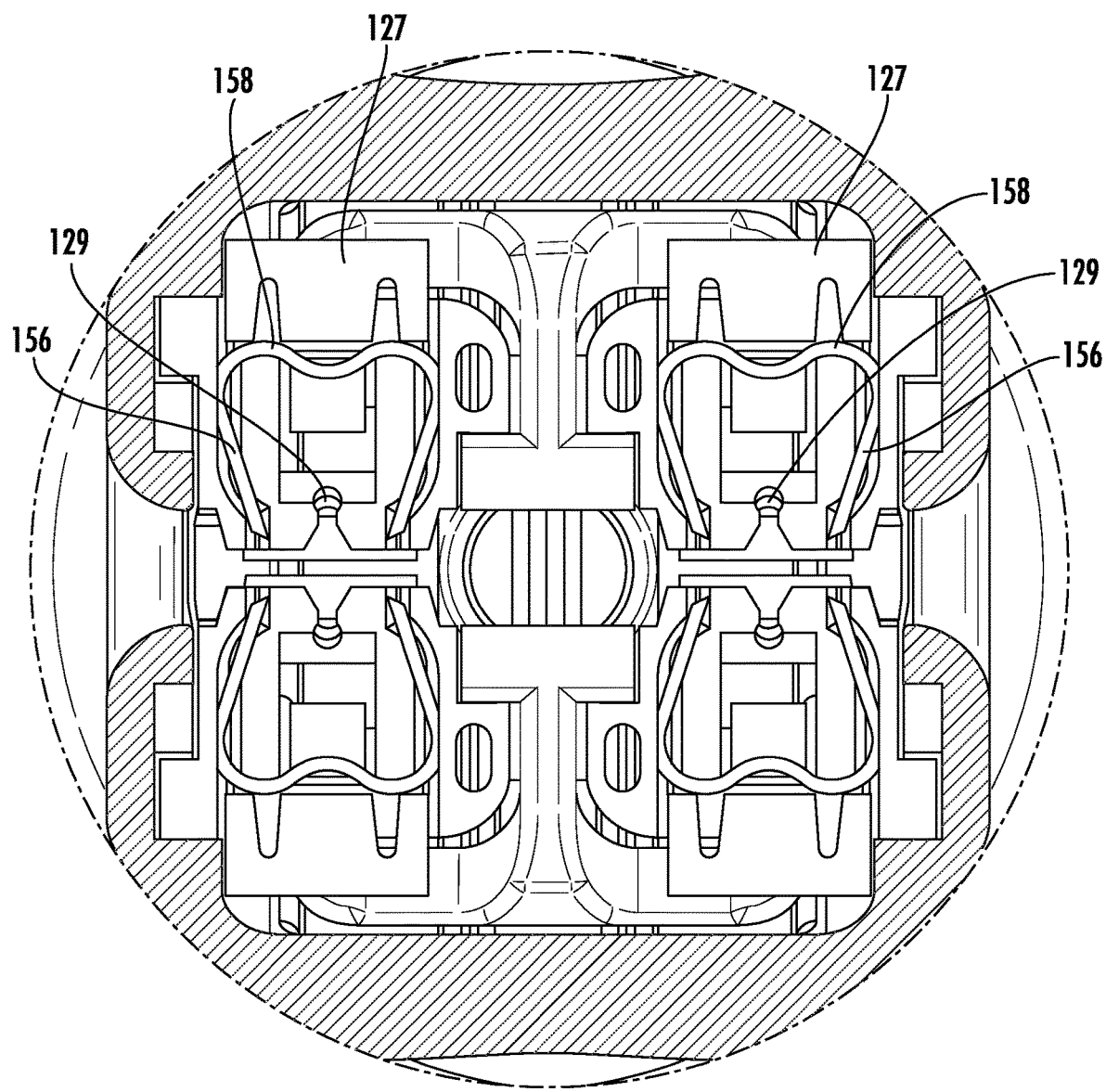
FIGS. 13A and 13B schematically show the firing of a staple to capture the suture and form a purse string.
Figure 13B:
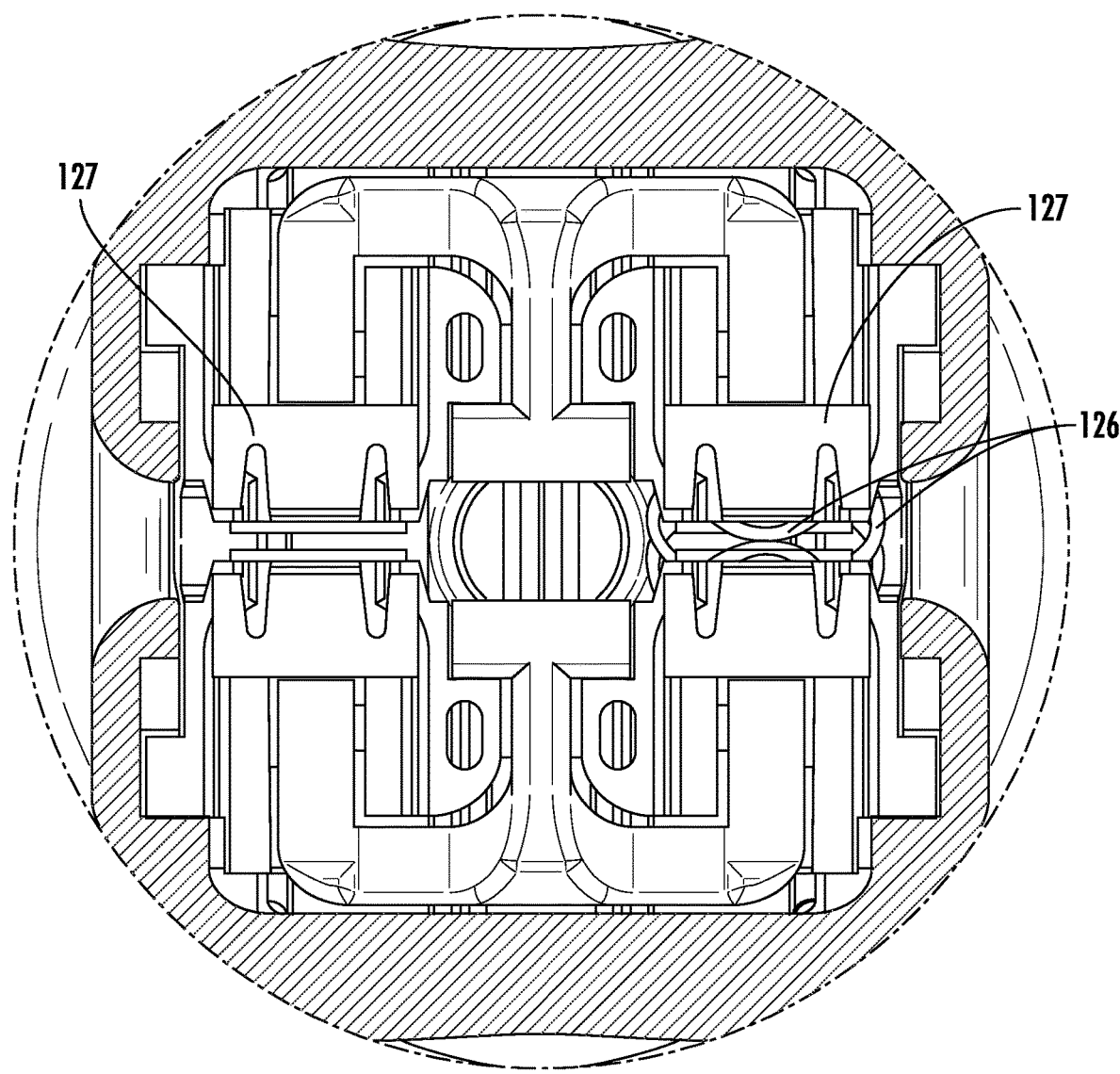

FIG. 13 shows shuttle 130 traveling distally during firing of surgical instrument 100. In FIG. 13, inclined distal portion 131 of shuttle 130 has fully deployed a first staple 126a and is engaging a second staple driver 127 to deploy a second staple 126b. As seen in FIGS. 13A and 13B, initially, each staple 126 is pushed under a force applied by a staple driver 127 to the backspan 158 of the staple while lateral forces are simultaneously applied against the legs 156 by the lips 157 of staple receiving pockets 128 so that the legs 156 begin to deform and move towards each other while penetrating into tissue 197. As depicted in FIG. 13B near the end of each stroke of staple drivers 127 the legs 156 of a staple have been substantially deformed so as to be in crossing relation to each other. In this position, the staples will not readily pull out from tissue 197. At the same time, sutures 129a, 129b are pushed out of channels 159a-d and are captured between the deformed staples 126 and tissue 197. Sutures 129 form a purse string as they are retained within the deformed staples 126.

Figure 14:
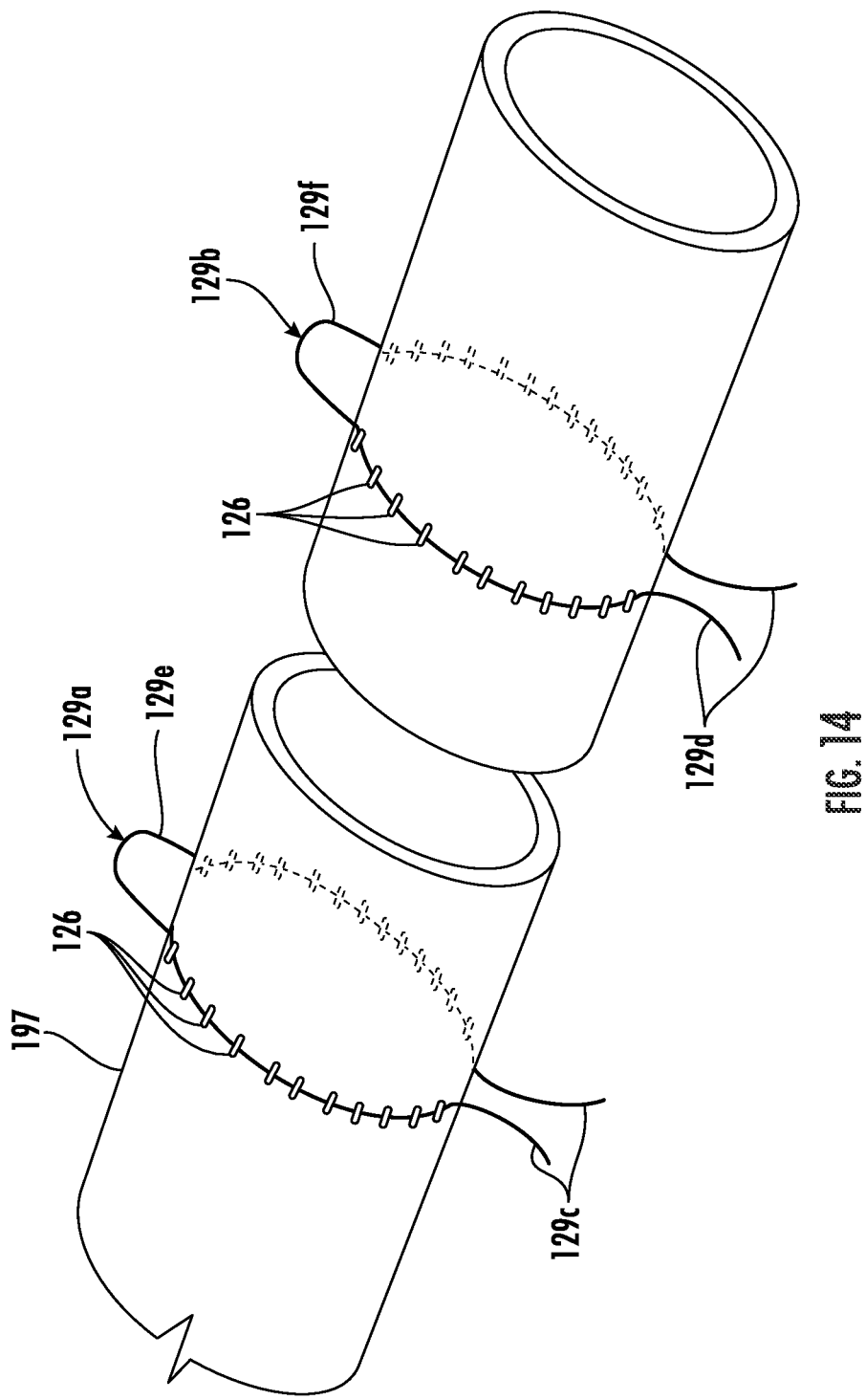
FIG. 14 depicts an illustrative vessel that has been severed and secured with a series of staples combined with sutures to form purse strings.

FIG. 14 depicts an illustrative blood vessel or tissue that has been severed and stapled with a surgical instrument in accordance with this disclosure. Sutures 129a, 129b have been secured to the tissue in a purse string formation with staples 126 holding sutures 129a, 129b in place. Once secured, another instrument may be used to cinch the purse string tight by pulling on the ends 129c, 129d. In embodiments, a clips 165a, 165b may be preloaded into distal end of cartridge 122 and secured to the ends 129c, 129d of sutures 129a, 129b and used to allow a surgeon to cinch the purse string tight by hand to retain the sutures 129a, 129b in the cinched configuration.

Figure 15:
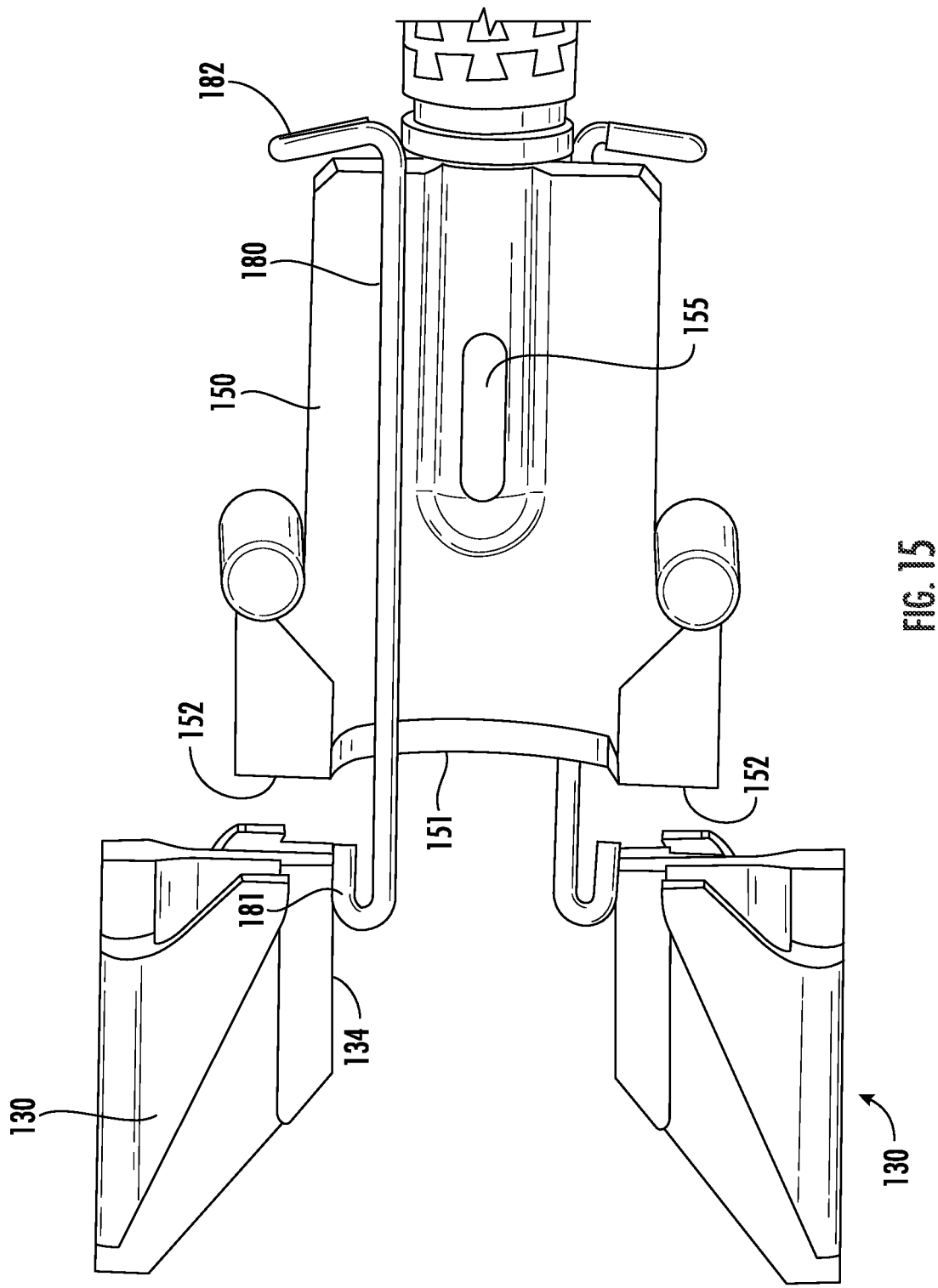
FIG. 15 depicts a locking mechanism suitable for use in the surgical instrument of FIG. 1 in a disabled configuration.
Figure 16:
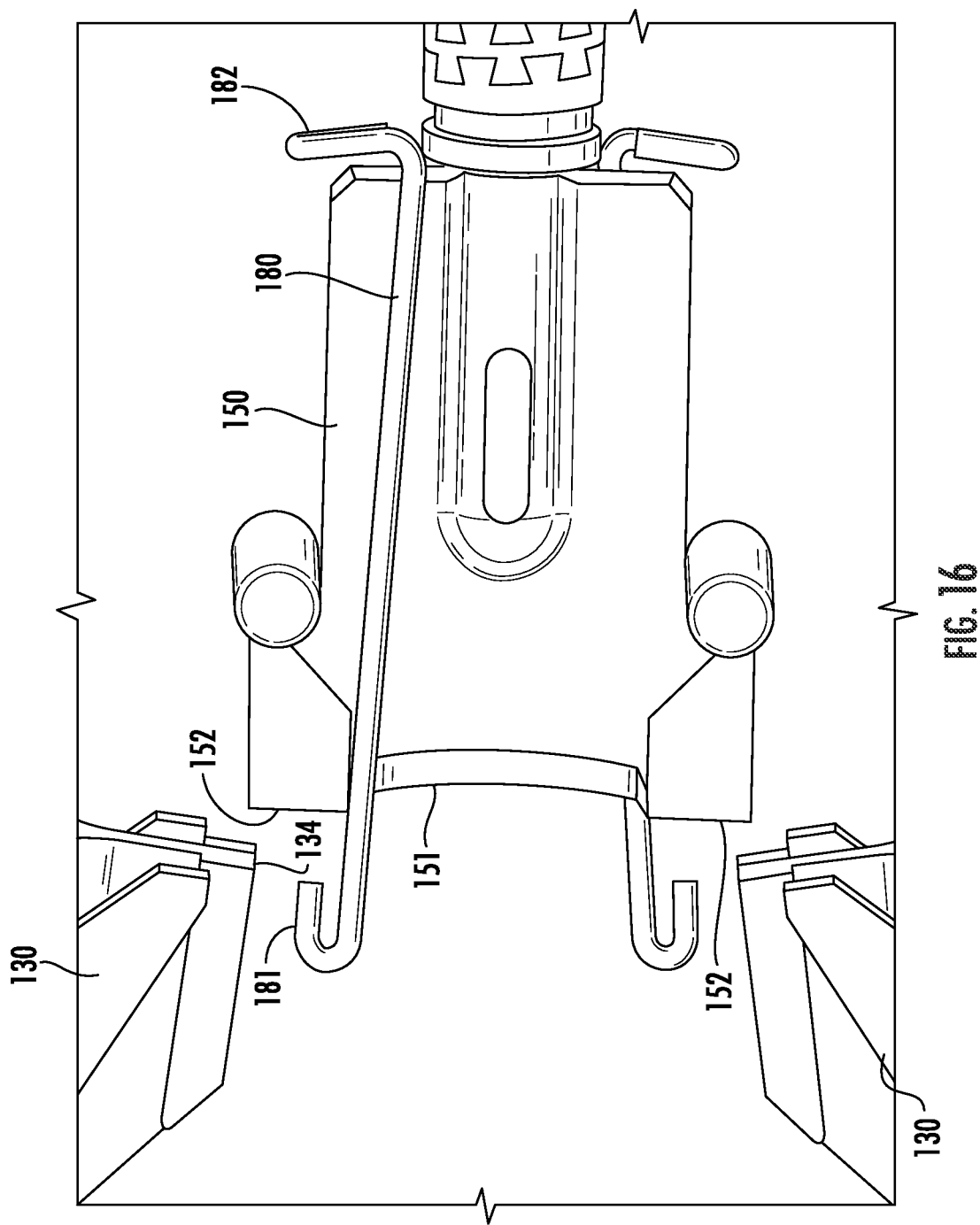
FIG. 16 depicts the locking mechanism of FIG. 15 in an enabled configuration.

FIGS. 15 and 16 show a lockout mechanism that may be used with surgical instruments in accordance with embodiments of this disclosure.

In FIG. 15, a disabled locking mechanism is shown. Locking member 180 has an engagement portion 181 on the distal end of locking member 180, and a proximal portion 182 on the proximal end of locking member 180. In embodiments, distal portion 181 of locking member 180 is shaped like a hook. In embodiments, locking member 180 is formed from spring wire. When an unfired cartridge is installed, inner edge 134 of shuttle 130 contacts engagement portion 181 of locking member 180, keeping it out of alignment with distal edges 152 of drive member 150. In this position, drive member 150 may be translated distally allowing a user to actuate the instrument.

FIG. 16 shows an enabled locking mechanism. Locking member 180 is designed such that engagement portion 181 is biased towards a position that aligns engagement portion 181 with distal edges 152 of drive member 150. As seen in FIG. 16, when shuttle 130 is moved and inner edge 134 of shuttle 130 no longer contacts locking member 180, engagement portion 181 of locking member 180 moves back to its naturally biased position, where it is aligned with distal edges 152 of drive member 150. Once the instrument is fired and retraction of drive member 150 occurs, a user may not fire the instrument again without installing a fresh unfired cartridge, as distal edges 152 will contact engagement portion 181 of locking member 180 and the drive member 150 will be prevented from translating distally unless a fresh cartridge is installed, and the jaws have closed sufficiently such that they are parallel and clamped on tissue.

Figure 17:
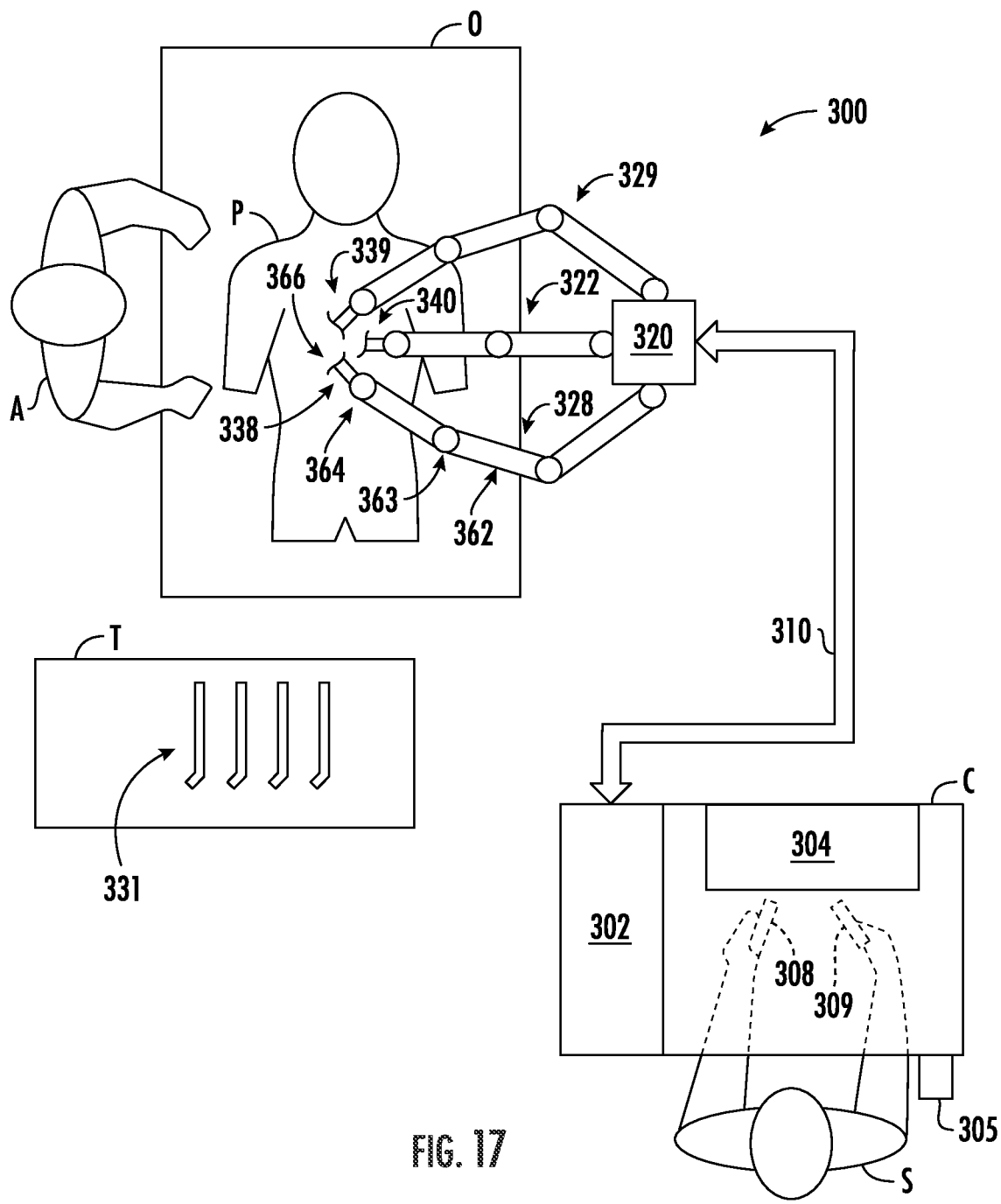
FIG. 17 illustrates a top view of an operating room employing a robotic surgical system utilizing aspects of the present disclosure.

The present surgical instrument for applying one or more purse string sutures may be used in a robotic surgical system. FIG. 17 illustrates, as an example, a top view of an operating room employing a robotic surgical system. The robotic surgical system in this case is a robotic surgical system 300 including a Console ("C") utilized by a Surgeon ("S") while performing a minimally invasive diagnostic or surgical procedure, usually with assistance from one or more Assistants ("A"), on a Patient ("P") who is lying down on an Operating table ("O").

The Console includes a monitor 304 for displaying an image of a surgical site to the Surgeon, left and right manipulatable control devices 308 and 309, a foot pedal 305, and a processor 302. The control devices 308 and 309 may include any one or more of a variety of input devices such as joysticks, gloves, trigger-guns, hand-operated controllers, or the like. The processor 302 may be a dedicated computer that may be integrated into the Console or positioned next to it.

The Surgeon performs a minimally invasive surgical procedure by manipulating the control devices 308 and 309 (also referred to herein as "master manipulators") so that the processor 302 causes their respectively associated robotic arm assemblies, 328 and 329, (also referred to herein as "slave manipulators") to manipulate their respective removably coupled surgical instruments 338 and 339 (also referred to herein as "tools") accordingly, while the Surgeon views the surgical site in 3-D on the Console monitor 304 as it is captured by a stereoscopic endoscope 340.

Each of the tools 338 and 339, as well as the endoscope 340, may be inserted through a cannula or other tool guide (not shown) into the Patient so as to extend down to the surgical site through a corresponding minimally invasive incision such as incision 366. Each of the robotic arms is conventionally formed of links, such as link 362, which are coupled together and manipulated through motor controlled or active joints, such as joint 363.

The number of surgical tools used at one time and consequently, the number of robotic arms being used in the system 300 will generally depend on the diagnostic or surgical procedure and the space constraints within the operating room, among other factors. If it is necessary to change one or more of the tools being used during a procedure, the Assistant may remove the tool no longer being used from its robotic arm, and replace it with another tool 331 from a Tray ("T") in the operating room.

The monitor 304 may be positioned near the Surgeon's hands so that it will display a projected image that is oriented so that the Surgeon feels that he or she is actually looking directly down onto the operating site. To that end, images of the tools 338 and 339 may appear to be located substantially where the Surgeon's hands are located.

The processor 302 performs various functions in the system 300. One important function that it performs is to translate and transfer the mechanical motion of control devices 308 and 309 to their respective robotic arms 328 and 329 through control signals over bus 310 so that the Surgeon can effectively manipulate their respective tools 338 and 339. Another important function is to implement various control system processes as described herein.

Although described as a processor, it is to be appreciated that the processor 302 may be implemented in practice by any combination of hardware, software and firmware. Also, its functions as described herein may be performed by one unit, or divided up among different components, each of which may be implemented in turn by any combination of hardware, software and firmware.

For additional details on robotic surgical systems, see, e.g., U.S. Pat. Nos. 6,493,608 and 6,671,581, the entire contents of which are incorporated herein by this reference.

Figure 18:
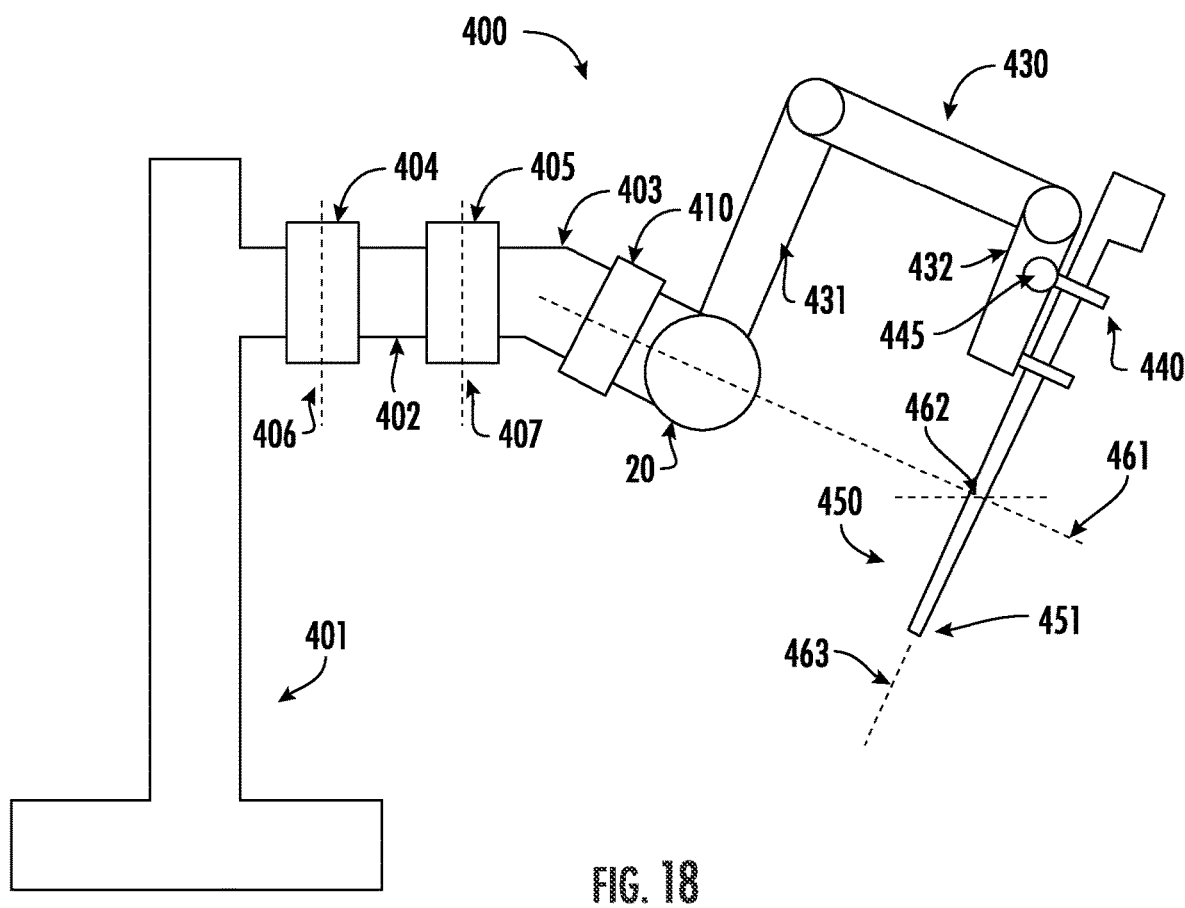
FIG. 18 illustrates a simplified side view of a robotic arm assembly that is usable with various aspects of the present disclosure.

FIG. 18 illustrates, as an example, a side view of a simplified (not necessarily in proportion or complete) illustrative robotic arm assembly 400 (which is representative of robotic arm assemblies 328 and 329) holding a surgical instrument 450 (which is representative of tools 338 and 339) for performing a surgical procedure. The surgical instrument 450 is removably held in tool holder 440. The arm assembly 400 is mechanically supported by a base 401, which may be part of a patient-side movable cart or affixed to the operating table or ceiling. It includes links 402 and 403 which are coupled together and to the base 401 through setup joints 404 and 405.

The setup joints 404 and 405 in this example are passive joints that allow manual positioning of the arm 400 when their brakes are released. For example, setup joint 404 allows link 402 to be manually rotated about axis 406, and setup joint 405 allows link 403 to be manually rotated about axis 407.

Although only two links and two setup joints are shown in this example, more or less of each may be used as appropriate in this and other robotic arm assemblies in conjunction with the present invention. For example, although setup joints 404 and 405 are useful for horizontal positioning of the arm 400, additional setup joints may be included and useful for limited vertical and angular positioning of the arm 400. For major vertical positioning of the arm 400, however, the arm 400 may also be slidably moved along the vertical axis of the base 401 and locked in position.

The robotic arm assembly 400 also includes three active joints driven by motors. A yaw joint 410 allows arm section 430 to rotate around an axis 461, and a pitch joint 420 allows arm section 430 to rotate about an axis perpendicular to that of axis 461 and orthogonal to the plane of the drawing. The arm section 430 is configured so that sections 431 and 432 are always parallel to each other as the pitch joint 420 is rotated by its motor. As a consequence, the instrument 450 may be controllably moved by driving the yaw and pitch motors so as to pivot about the pivot point 462, which is generally located through manual positioning of the setup joints 404 and 405 so as to be at the point of incision into the patient. In addition, an insertion gear 445 may be coupled to a linear drive mechanism (not shown) to extend or retract the instrument 450 along its axis 463.

Although each of the yaw, pitch and insertion joints or gears, 410, 420 and 445, is controlled by an individual joint or gear controller, the three controllers are controlled by a common master/slave control system so that the robotic arm assembly 400 (also referred to herein as a "slave manipulator") may be controlled through user (e.g., surgeon) manipulation of its associated master manipulator.

While several embodiments have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of presently disclosed embodiments. Thus, the scope of the embodiments should be determined by the appended claims and their legal equivalents, rather than by the examples given.

Persons skilled in the art will understand that the devices and methods specifically described herein and illustrated in the accompanying drawings are non-limiting exemplary embodiments. The features illustrated or described in connection with one exemplary embodiment may be combined with the features of other embodiments. Various alternatives and modifications can be devised by those skilled in the art without departing from the disclosure. Accordingly, the present disclosure is intended to embrace all such alternatives, modifications and variances. As well, one skilled in the art will appreciate further features and advantages of the present disclosure based on the above-described embodiments. Accordingly, the present disclosure is not to be limited by what has been particularly shown and described, except as indicated by the appended claims.

The invention claimed is:

1. A surgical stapler for applying a suture to tissue, the surgical stapler comprising:
an elongated shaft having a distal end and a proximal end;
an end effector having first and second jaws configured to move from an open position to a closed position;
a cartridge removably coupled to the end effector and having a first upper portion sized to fit into the first jaw, a second lower portion sized to fit into the second jaw and a living hinge between the first upper portion and the second lower portion, wherein the living hinge comprises a channel for receiving a suture, wherein the channel is configured to form the suture into a loop;
a drive member configured to translate distally through the end effector to apply staples and the suture to tissue; and
an actuation mechanism configured to translate the drive member distally through the end effector.

2. The surgical stapler of claim 1, wherein the drive member is configured to engage a plurality of staple drivers in the cartridge for ejecting staples such that the suture, in combination with the staples, forms a purse string with the tissue.

3. The surgical stapler of claim 1, wherein the upper and lower portions of the cartridge each include two rows of staples and are configured for installation upon a longitudinal axis of the end effector.

4. The surgical stapler of claim 1, wherein the cartridge further comprises a distal portion configured to retain the cartridge in the first and second jaws.

5. The surgical stapler of claim 1, wherein the first and second jaws are configured to move from the open position, to a partially closed position, wherein the jaws are substantially parallel with each other and define a gap therebetween.

6. The surgical stapler of claim 5, wherein the first and second jaws include cam slots having a first jaw-closing portion for allowing the jaws to move from the open position to the partially closed position and second jaw-closing portion for allowing the jaws to move from the partially closed position to the closed position.

7. The surgical stapler of claim 1 further comprising an actuator operatively connected to the actuation mechanism, wherein the actuator includes a control device of a robotic surgical system.

8. A surgical stapler for applying a suture to tissue, the surgical stapler comprising:
an elongated shaft having distal and proximal ends;
an end effector having first and second jaws configured to receive a cartridge;
a drive member configured to translate distally through the end effector to apply staples and a suture to tissue;
an actuation mechanism configured to translate the drive member distally through the end effector; and
wherein the first and second jaws are movable between an open position, wherein the jaws define an angle therebetween, to a partially closed position, wherein the jaws are substantially parallel with each other and define a gap therebetween, to a closed position, wherein the jaw are substantially parallel to each other and wherein at least one of the first and second jaws includes a cam slot having a first jaw-closing portion for allowing the jaws to move from the open position to the partially closed position and second jaw-closing portion for allowing the jaws to move from the partially closed position to the closed position.

9. The surgical stapler of claim 8, wherein the end effector defines a longitudinal axis and wherein the first jaw-closing portion of the cam slot extends at a transverse angle to the longitudinal axis and the second jaw-closing portion of the cam slot is substantially parallel to the longitudinal axis.

10. The surgical stapler of claim 8, further comprising:
at least one link member configured to rotate about at least one pivot pin upon application of force to the link member; and
a cam slot pin extending from the link member and through the cam slot, wherein the cam slot pin is configured to translate through the cam slot upon rotation of the link member.

11. The surgical stapler of claim 10, further comprising a drive cable configured to apply a force to the link member to cause rotation about the pivot pin.

12. The surgical stapler of claim 10, wherein the cam slot is disposed in the second jaw, the first jaw comprising a pivot hole and the link member comprising a proximal pin that extends through the pivot hole.

13. The surgical stapler of claim 8, wherein the drive member is configured to engage a plurality of staple drivers in the cartridge for ejecting the staples such that the suture, in combination with the staples, forms a purse string with the tissue.

14. The surgical stapler of claim 8 further comprising an actuator operatively connected to the actuation mechanism, wherein the actuator includes a control device of a robotic surgical system.

15. The surgical stapler of claim 8, wherein the drive member engages the staples as the jaws move from the partially closed position to the closed position.

16. A surgical stapler for applying a suture to tissue, the surgical stapler comprising:
an elongated shaft having a distal end and a proximal end;
an end effector having first and second jaws configured to move between an open position and a closed position;
a drive member configured to translate distally through the end effector to apply staples and a suture to tissue, the drive member comprises a cutting element and at least one inclined surface
a link member coupled to the first and second jaws and configured to rotate about at least one pivot pin to open and close the jaws, wherein the link member comprises at least one drive pin;
wherein the end effector comprises a drive pin slot for receiving the drive pin; and
wherein distal translation of the drive member causes the inclined surface to engage the drive pin and translate the drive pin through the drive pin slot to move the jaws from the open position to the closed position.

* * * * *